US012637265B2

(12) United States Patent
Doornbos et al.

(10) Patent No.: US 12,637,265 B2
(45) Date of Patent: May 26, 2026

(54) VENTED FLUID TRANSFER LID

(71) Applicant: Avent, Inc., Alpharetta, GA (US)

(72) Inventors: David A. Doornbos, Woodstock, GA
(US); Mariann Cary, Canton, GA
(US); Benjamin M. Davis, Woodstock,
GA (US)

(73) Assignee: Avent, Inc., Alpharetta, GA (US)

( * ) Notice: Subject to any disclaimer, the term of this
patent is extended or adjusted under 35
U.S.C. 154(b) by 70 days.

(21) Appl. No.: 18/341,212

(22) Filed: Jun. 26, 2023

(65) Prior Publication Data

US 2023/0331444 A1     Oct. 19, 2023

Related U.S. Application Data

(63) Continuation of application No. 15/782,695, filed on
Oct. 12, 2017, now abandoned.

(Continued)

(51) Int. Cl.
B65D 47/32         (2006.01)
A61J 1/14          (2023.01)
(Continued)

(52) U.S. Cl.
CPC .......... B65D 47/143 (2013.01); A61J 1/1418
(2015.05); A61J 1/1481 (2015.05); **A61J
1/1487** (2015.05);
(Continued)

(58) Field of Classification Search
CPC .. A61J 9/085; A61J 1/1418; A61J 1/00; A61J
1/05; A61J 1/1412; A61J 1/1425;
(Continued)

(56) References Cited

U.S. PATENT DOCUMENTS

| | | | | |
|---|---|---|---|---|
| 2,477,598 A | | 8/1949 | Hain | |
| 3,147,876 A | * | 9/1964 | Lepore | B65D 51/1622 |
| | | | | 215/261 |

(Continued)

FOREIGN PATENT DOCUMENTS

| | | |
|---|---|---|
| DE | 7740288 U1 | 5/1978 |
| DE | 3217913 A1 | 12/1983 |

(Continued)

OTHER PUBLICATIONS

Alex Tabenkin, To Each His Own Parameter, Jun. 2001, Quality
Digest, Jun. 2001 Edition, accessed Dec. 10, 2024 (Year: 2001).*

(Continued)

*Primary Examiner* — Allan D Stevens
(74) *Attorney, Agent, or Firm* — Meunier Carlin &
Curfman LLC

(57)                ABSTRACT

A vented transfer lid includes an inner collar projecting from
a top panel of the transfer lid and having an outer circum-
ferential surface having a texturized electrical discharge
machining (EDM) surface finish. In some example forms, an
interior surface of the top panel includes a texturized EDM
surface finish. In example forms, the transfer lid includes a
transfer port wherein at least a portion of an interior surface
of the transfer port includes a texturized EDM surface finish.
In other embodiments, at least a portion of the vented
transfer lid comprises a nonpolar boundary such that fluids
exposed to the nonpolar boundary bead and form droplets
having a dimension rendering them incapable of passing
through one or more vent paths.

13 Claims, 13 Drawing Sheets

Related U.S. Application Data

(60) Provisional application No. 62/516,908, filed on Jun. 8, 2017, provisional application No. 62/407,140, filed on Oct. 12, 2016.

(51) Int. Cl.

| | |
|---|---|
| *A61J 1/20* | (2006.01) |
| *A61J 9/08* | (2006.01) |
| *B65D 47/06* | (2006.01) |
| *B65D 47/14* | (2006.01) |
| *A61M 1/06* | (2006.01) |
| *B67D 3/00* | (2006.01) |
| *C23C 16/44* | (2006.01) |

(52) U.S. Cl.
CPC ........... *A61J 1/2075* (2015.05); *A61J 1/2096* (2013.01); *A61J 9/085* (2013.01); *B65D 47/06* (2013.01); *B65D 47/32* (2013.01); *A61J 1/1468* (2015.05); *A61M 1/062* (2014.02); *B67D 3/0041* (2013.01); *C23C 16/4412* (2013.01)

(58) Field of Classification Search
CPC ...... A61J 1/1475; A61J 1/1481; A61J 1/1487; B65D 47/06; B65D 47/061; B65D 47/063; B65D 47/065; B65D 47/066; B65D 47/068; B65D 47/08; B65D 47/0804; B65D 47/0809; B65D 47/0814; B65D 47/0819; B65D 47/0823; B65D 47/0828; B65D 47/0833; B65D 47/0838; B65D 47/0842; B65D 47/0847; B65D 47/0852; B65D 47/0857; B65D 47/0861; B65D 47/0866; B65D 47/0871; B65D 47/0876; B65D 47/088; B65D 47/0885; B65D 47/089; B65D 47/0895; B65D 47/10; B65D 47/103; B65D 47/106; B65D 47/12; B65D 47/121; B65D 47/122; B65D 47/123; B65D 47/125; B65D 47/126; B65D 47/127; B65D 47/128; B65D 47/14; B65D 47/141; B65D 47/142; B65D 47/143; B65D 47/145; B65D 47/146; B65D 47/147; B65D 47/148; B65D 47/16; B65D 47/18; B65D 47/185; B65D 47/32
USPC ......................................................... 215/261
See application file for complete search history.

(56) References Cited

U.S. PATENT DOCUMENTS

| | | | |
|---|---|---|---|
| 3,307,752 | A | 3/1967 | Anderson |
| 3,344,786 | A | 10/1967 | Berg et al. |
| 3,468,309 | A | 9/1969 | Drewe |
| 3,473,833 | A | 10/1969 | Bremer |
| 3,572,337 | A | 3/1971 | Schunk |
| 3,712,749 | A | 1/1973 | Roberts |
| 3,904,062 | A | 9/1975 | Grussen |
| 3,937,211 | A | 2/1976 | Merten |
| 4,043,334 | A | 8/1977 | Brown et al. |
| 4,046,145 | A | 9/1977 | Choksi et al. |
| 4,286,591 | A | 9/1981 | Raines |
| 4,303,071 | A | 12/1981 | Smith |
| 4,449,640 | A | 5/1984 | Finkelstein |
| 4,493,348 | A | 1/1985 | Lemmons |
| 4,508,236 | A | 4/1985 | Keilman et al. |
| 4,685,173 | A | 8/1987 | Pavur |
| 4,717,386 | A | 1/1988 | Simmons |
| 4,743,229 | A | 5/1988 | Chu |
| 4,760,941 | A | 8/1988 | Salmon et al. |
| 4,772,152 | A | 9/1988 | Gill |
| 4,842,592 | A | 6/1989 | Caggiani et al. |
| D303,710 | S | 9/1989 | Neill |
| 4,883,483 | A | 11/1989 | Lindmayer |
| 4,944,736 | A | 7/1990 | Holtz |
| D309,710 | S | 8/1990 | Groves |
| D310,028 | S | 8/1990 | Brandt et al. |
| 4,994,044 | A | 2/1991 | Lo Duca |
| 4,997,429 | A | 3/1991 | Dickerhoff et al. |
| 5,078,733 | A | 1/1992 | Eveleigh et al. |
| 5,090,583 | A | 2/1992 | Hoffman et al. |
| D327,318 | S | 6/1992 | Dudar et al. |
| 5,224,937 | A | 7/1993 | Van Der Heiden et al. |
| 5,238,130 | A | 8/1993 | Marques et al. |
| 5,242,423 | A | 9/1993 | Goodsir et al. |
| 5,275,619 | A | 1/1994 | Engebretson et al. |
| 5,328,058 | A | 7/1994 | Leoncavallo et al. |
| 5,356,406 | A | 10/1994 | Schraga |
| 5,405,339 | A | 4/1995 | Kohnen et al. |
| 5,429,256 | A | 7/1995 | Kestenbaum |
| 5,451,213 | A | 9/1995 | Teicher et al. |
| 5,451,374 | A | 9/1995 | Molina |
| 5,454,409 | A | 10/1995 | McAffer et al. |
| 5,484,070 | A | 1/1996 | Graham |
| 5,505,705 | A | 4/1996 | Galpin et al. |
| 5,507,416 | A | 4/1996 | Rapchak et al. |
| 5,509,911 | A | 4/1996 | Cottone, Sr. et al. |
| 5,573,516 | A | 11/1996 | Tyner |
| 5,573,525 | A | 11/1996 | Watson et al. |
| D378,233 | S | 2/1997 | Warner |
| 5,598,939 | A | 2/1997 | Watson et al. |
| 5,620,434 | A | 4/1997 | Brony |
| 5,624,402 | A | 4/1997 | Imbert |
| D395,502 | S | 6/1998 | Deily et al. |
| 5,788,099 | A | 8/1998 | Treu et al. |
| 5,797,885 | A | 8/1998 | Rubin |
| D398,060 | S | 9/1998 | Brown |
| 5,848,994 | A | 12/1998 | Richmond |
| 5,853,096 | A | 12/1998 | Bartur et al. |
| 5,871,500 | A | 2/1999 | Jepson et al. |
| 5,921,419 | A | 7/1999 | Niedospial, Jr. et al. |
| 5,924,584 | A | 7/1999 | Hellstrom et al. |
| 5,957,166 | A | 9/1999 | Safabash |
| 5,971,181 | A | 10/1999 | Niedospial, Jr. et al. |
| 6,056,135 | A | 5/2000 | Widman |
| 6,068,614 | A | 5/2000 | Kimber et al. |
| 6,106,502 | A | 8/2000 | Richmond |
| D432,916 | S | 10/2000 | Drinkwater et al. |
| D435,652 | S | 12/2000 | Nazarifar et al. |
| 6,168,037 | B1 | 1/2001 | Grimard |
| 6,270,519 | B1 | 8/2001 | Botts |
| 6,280,418 | B1 | 8/2001 | Reinhard et al. |
| 6,499,617 | B1 | 12/2002 | Niedospial, Jr. et al. |
| D473,647 | S | 4/2003 | Francavilla et al. |
| 6,550,626 | B1 * | 4/2003 | Randall ............. B65D 41/3442 |
| | | | 220/259.2 |
| D474,839 | S | 5/2003 | Francavilla et al. |
| 6,592,251 | B2 | 7/2003 | Edwards et al. |
| 6,632,199 | B1 | 10/2003 | Tucker et al. |
| 6,726,672 | B1 | 4/2004 | Hanly et al. |
| 6,749,092 | B2 | 6/2004 | Olechowski et al. |
| 6,821,267 | B2 | 11/2004 | Veillon, Jr. et al. |
| D528,910 | S | 9/2006 | Kingsley |
| D530,200 | S | 10/2006 | Kingsley |
| D534,796 | S | 1/2007 | Falkenburg |
| D547,657 | S | 7/2007 | Tacchella |
| 7,284,580 | B2 | 10/2007 | Dallison et al. |
| 7,316,669 | B2 | 1/2008 | Ranalletta |
| 7,387,216 | B1 | 6/2008 | Smith |
| 7,503,905 | B2 | 3/2009 | Jessop et al. |
| 7,523,967 | B2 | 4/2009 | Steppe |
| D596,487 | S | 7/2009 | Batton et al. |
| 7,594,681 | B2 | 9/2009 | DeCarlo |
| D602,355 | S | 10/2009 | Waaland |
| 7,666,170 | B2 | 2/2010 | Guala |
| 7,717,281 | B2 | 5/2010 | Baudin |
| D617,187 | S | 6/2010 | Murray |
| 7,740,288 | B2 | 6/2010 | Mantell |
| 7,766,919 | B2 | 8/2010 | Delmotte |
| 7,811,278 | B2 | 10/2010 | Knipple, Jr. et al. |

(56) References Cited

U.S. PATENT DOCUMENTS

| | | | |
|---|---|---|---|
| D627,899 S | 11/2010 | Cofie | |
| 7,857,284 B2 | 12/2010 | Kimball et al. | |
| D630,732 S | 1/2011 | Lev et al. | |
| 7,985,205 B2 | 7/2011 | Adams | |
| D644,618 S | 9/2011 | Morihira | |
| 8,016,795 B2 | 9/2011 | Barrelle et al. | |
| 8,051,997 B2 | 11/2011 | Buckley | |
| 8,099,932 B2 | 1/2012 | Peacop et al. | |
| 8,109,902 B2 | 2/2012 | Middleton et al. | |
| 8,152,790 B2 | 4/2012 | Lopez et al. | |
| 8,177,768 B2 | 5/2012 | Leinsing | |
| 8,245,870 B2 | 8/2012 | McKinney et al. | |
| 8,272,411 B2 | 9/2012 | Py | |
| 8,303,571 B2 | 11/2012 | Kraushaar et al. | |
| 8,328,768 B2 | 12/2012 | Quigley et al. | |
| D674,277 S | 1/2013 | Hanson et al. | |
| 8,343,041 B2 | 1/2013 | Byers et al. | |
| 8,398,607 B2 | 3/2013 | Fangrow, Jr. | |
| D682,688 S | 5/2013 | Murray | |
| 8,444,621 B2 | 5/2013 | Fremming et al. | |
| D684,055 S | 6/2013 | Kwon | |
| D684,057 S | 6/2013 | Kwon | |
| 8,459,312 B2 | 6/2013 | Manera et al. | |
| D686,339 S | 7/2013 | Shima et al. | |
| D686,495 S | 7/2013 | Murray | |
| 8,479,370 B2 | 7/2013 | Grant | |
| 8,528,757 B2 | 9/2013 | Bisio | |
| 8,529,524 B2 | 9/2013 | Newton et al. | |
| D691,261 S | 10/2013 | Kawamura | |
| D692,143 S | 10/2013 | Shahidi Bonjar | |
| 8,551,068 B2 | 10/2013 | Kyle et al. | |
| D693,923 S | 11/2013 | Hernandez et al. | |
| 8,613,738 B2 | 12/2013 | Mantell | |
| 8,641,685 B2 | 2/2014 | Mansour et al. | |
| 8,679,090 B2 | 3/2014 | Anderson et al. | |
| D705,061 S | 5/2014 | Jo et al. | |
| D706,135 S | 6/2014 | Hutchison et al. | |
| 8,753,325 B2 | 6/2014 | Lev et al. | |
| 8,758,322 B2 | 6/2014 | McCoy et al. | |
| D710,695 S | 8/2014 | Pritikin | |
| D712,025 S | 8/2014 | Kawamura | |
| D712,744 S | 9/2014 | Neputy et al. | |
| D713,247 S | 9/2014 | Webster et al. | |
| D714,142 S | 9/2014 | Hojo | |
| D714,935 S | 10/2014 | Nishioka et al. | |
| D715,143 S | 10/2014 | Hewitt et al. | |
| D715,146 S | 10/2014 | Holmes | |
| 8,852,167 B2 | 10/2014 | Trombley, III et al. | |
| 8,870,834 B2 | 10/2014 | Milijasevic | |
| D716,636 S | 11/2014 | McDonald | |
| D717,948 S | 11/2014 | Strong et al. | |
| 8,926,840 B2 | 1/2015 | Hull et al. | |
| D723,181 S | 2/2015 | Kawamura | |
| D725,284 S | 3/2015 | Karlsson et al. | |
| D726,308 S | 4/2015 | Shubin, Sr. et al. | |
| 9,016,473 B2 | 4/2015 | Tamarindo | |
| 9,017,295 B2 | 4/2015 | Pan | |
| 9,033,938 B2 | 5/2015 | Milijasevic | |
| D731,065 S | 6/2015 | Winter | |
| D731,647 S | 6/2015 | Nishioka et al. | |
| D735,038 S | 7/2015 | Tamarindo | |
| 9,073,021 B2 | 7/2015 | Nakamura et al. | |
| D736,914 S | 8/2015 | Schultz | |
| D736,915 S | 8/2015 | Schultz | |
| 9,095,500 B2 | 8/2015 | Brandenburger et al. | |
| D737,962 S | 9/2015 | Schultz | |
| 9,126,029 B2 | 9/2015 | Fangrow et al. | |
| D741,996 S | 10/2015 | Strong et al. | |
| 9,149,623 B1 | 10/2015 | Colman | |
| 9,156,569 B2 | 10/2015 | Vassallo et al. | |
| 9,205,243 B2 | 12/2015 | Lopez et al. | |
| 9,205,248 B2 | 12/2015 | Wu et al. | |
| 9,289,587 B2 | 3/2016 | Colman | |
| 9,296,531 B2 | 3/2016 | Luzbetak et al. | |
| D756,200 S | 5/2016 | McDonald | |
| 9,345,639 B2 | 5/2016 | Ferrara | |
| 9,345,642 B2 | 5/2016 | Heath et al. | |
| D759,486 S | 6/2016 | Ingram et al. | |
| 9,427,715 B2 | 8/2016 | Palazzolo et al. | |
| 9,433,562 B2 | 9/2016 | Ingram et al. | |
| 9,656,022 B1 * | 5/2017 | Russo | A61M 5/31576 |
| 9,724,270 B2 | 8/2017 | Bonnal et al. | |
| 9,776,779 B2 | 10/2017 | Campbell | |
| D802,743 S | 11/2017 | Davis et al. | |
| 9,907,728 B2 | 3/2018 | Kyle et al. | |
| 2003/0088232 A1 | 5/2003 | Duell | |
| 2005/0055008 A1 | 3/2005 | Paradis et al. | |
| 2005/0165351 A1 | 7/2005 | Tamagni, Jr. | |
| 2005/0209555 A1 | 9/2005 | Middleton et al. | |
| 2006/0108319 A1 | 5/2006 | Meittunen | |
| 2006/0217679 A1 | 9/2006 | Hanly et al. | |
| 2007/0076041 A1 | 4/2007 | Carrez et al. | |
| 2007/0214692 A1 | 9/2007 | Ferrara | |
| 2008/0015539 A1 | 1/2008 | Pieroni et al. | |
| 2008/0183153 A1 | 7/2008 | Enns | |
| 2008/0312640 A1 | 12/2008 | Grant | |
| 2009/0230075 A1 | 9/2009 | Springer | |
| 2009/0321611 A1 | 12/2009 | Moberg | |
| 2010/0022951 A1 | 1/2010 | Ferrera et al. | |
| 2010/0252564 A1 | 10/2010 | Martinez et al. | |
| 2011/0054436 A1 | 3/2011 | Griffis, III et al. | |
| 2011/0130740 A1 | 6/2011 | Levy | |
| 2012/0018318 A1 | 1/2012 | Otsuka et al. | |
| 2012/0065608 A1 | 3/2012 | Costello et al. | |
| 2012/0103470 A1 | 5/2012 | Williger et al. | |
| 2012/0104054 A1 | 5/2012 | Terwilliger et al. | |
| 2012/0216909 A1 | 8/2012 | Levy | |
| 2014/0246616 A1 | 9/2014 | Fangrow | |
| 2014/0276466 A1 | 9/2014 | Yeh et al. | |
| 2014/0276651 A1 | 9/2014 | Schultz | |
| 2014/0323995 A1 | 10/2014 | Clauson et al. | |
| 2015/0238387 A1 | 8/2015 | Caetano | |
| 2016/0001056 A1 | 1/2016 | Nelson et al. | |
| 2016/0015601 A1 | 1/2016 | Davidson | |
| 2016/0030293 A1 | 2/2016 | Dorsey et al. | |
| 2016/0038374 A1 | 2/2016 | Merhold et al. | |
| 2016/0067147 A1 | 3/2016 | Davis et al. | |
| 2016/0067422 A1 | 3/2016 | Davis et al. | |
| 2016/0067471 A1 | 3/2016 | Ingram et al. | |
| 2016/0081878 A1 | 3/2016 | Marks et al. | |
| 2016/0143815 A1 | 5/2016 | Koelper et al. | |
| 2016/0159635 A1 | 6/2016 | Davis et al. | |
| 2016/0206845 A1 | 7/2016 | Colman et al. | |
| 2016/0367439 A1 | 12/2016 | Davis et al. | |
| 2017/0014616 A1 | 1/2017 | Davis et al. | |
| 2017/0173321 A1 | 6/2017 | Davis et al. | |
| 2017/0239141 A1 | 8/2017 | Davis et al. | |
| 2017/0320643 A1 | 11/2017 | Green | |

FOREIGN PATENT DOCUMENTS

| | | | |
|---|---|---|---|
| DE | 8613738 U1 | 7/1986 | |
| DE | 20302788 U1 | 6/2004 | |
| DE | 10200503510 A1 | 1/2007 | |
| EP | 0960616 A2 | 12/1999 | |
| EP | 2269685 A2 | 1/2011 | |
| EP | 3042691 A1 | 7/2016 | |
| FR | 2930428 A1 | 10/2009 | |
| FR | 2980971 A1 | 4/2013 | |
| JP | H10297655 A | 11/1998 | |
| JP | 4743229 B2 | 8/2011 | |
| WO | WO 9200717 A1 | 1/1992 | |
| WO | WO 9803210 A2 | 1/1998 | |
| WO | WO 9846278 A1 | 10/1998 | |
| WO | WO 9932155 A2 | 7/1999 | |
| WO | WO 2005065767 A2 | 7/2005 | |
| WO | WO 2008128074 A2 | 10/2008 | |
| WO | WO 2009068987 A1 | 6/2009 | |
| WO | WO 2009090627 A1 | 7/2009 | |
| WO | WO 2013081699 A2 | 6/2013 | |
| WO | WO 2014160911 A1 | 1/2014 | |
| WO | WO 2014049097 A1 | 4/2014 | |

(56) References Cited

FOREIGN PATENT DOCUMENTS

| WO | WO 2015034045 A1 | 3/2015 |
|---|---|---|
| WO | WO 2016089869 A1 | 6/2016 |

OTHER PUBLICATIONS

Alternative Syringes Low Displacement Option PowerPoint Presentation; Presented by Rork Swisher of Covidien: ISO 80369 Series Meeting; Berlin Germany; 11 pgs; Mar. 19, 2014.
Baxa Adapta-Cap Bottle Adapter; 1 pg; date unknown.
Baxa (Baxter) RAPIDFILL Connector; date unknown; 1 pg.
CareFusion Universal Vented Vial Adapter; 2 pgs; 2013.
Comar Tip Caps; date unknown; 1 pg.
Covidien ENFit Coupling; Mar. 2014; 1 pg.
International Search Report & Written Opinion for PCT/US2015/064237; 12 pgs; Mar. 3, 2016.
International Search Report & Written Opinion for PCT/US2015/048380; Oct. 29, 2015; 10 pgs.
International Search Report & Written Opinion for PCT/US2016/023771; Jun. 27, 2016; 17 pgs.
International Search Report & Written Opinion for PCT/US2016/038051; Sep. 2, 2016; 13 pgs.
International Search Report & Written Opinion for PCT/US2016/042514; Nov. 10, 2016; 12 pgs.
International Search Report & Written Opinion for PCT/US2017/01902 1; Sep. 22, 2017; 20 pgs.
International Search Report & Written Opinion for PCT/US2017/056391; Jan. 18, 2018; 16 pgs.
Invitation to Pay Additional Fees for PCT/US2017/019021; Jun. 6, 2017; 12 pgs.
Medela Breastmilk Transfer Lid; 1 pg: date unknown.
Medi-Dose EPS Press-In Bottle Adapters; 1 pg; date unknown.
NeoMed Self-Righting Tip Cap; date unknown; 1 pg.
New ISO Tubing Connector Standards: A Follow-Up to the Sentinel Event Alert Webinar PowerPoint Presentation; www.jointcommission.org; 50 pgs; Dec. 3, 2014.
New Tube Feeding Connectors Webinar PowerPoint Presentation; www.oley.org; 24 pgs; Jun. 24, 2014.
Specialty Medical Products Coupling (Item Code SMP-SCFF); Apr. 10, 2014; 1 pg.
Total Pharmacy Supply Bottle Adapter Plug; 1 pg; date unknown.
Total Pharmacy Supply Universal Bottle Adapter; 1 pg; date unknown.
WestPharma Vial Adapters; 2 pgs; 2014.

* cited by examiner

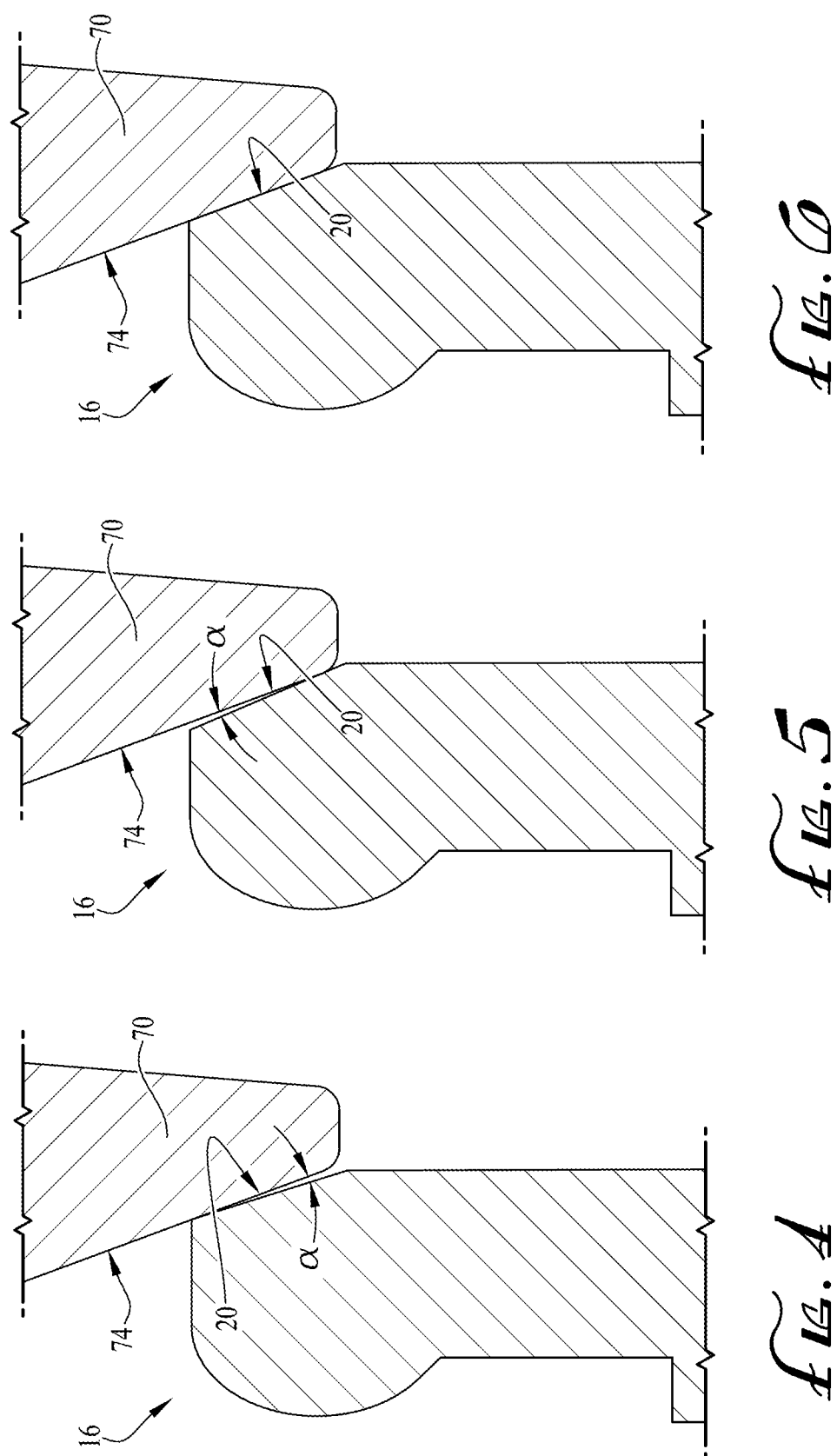

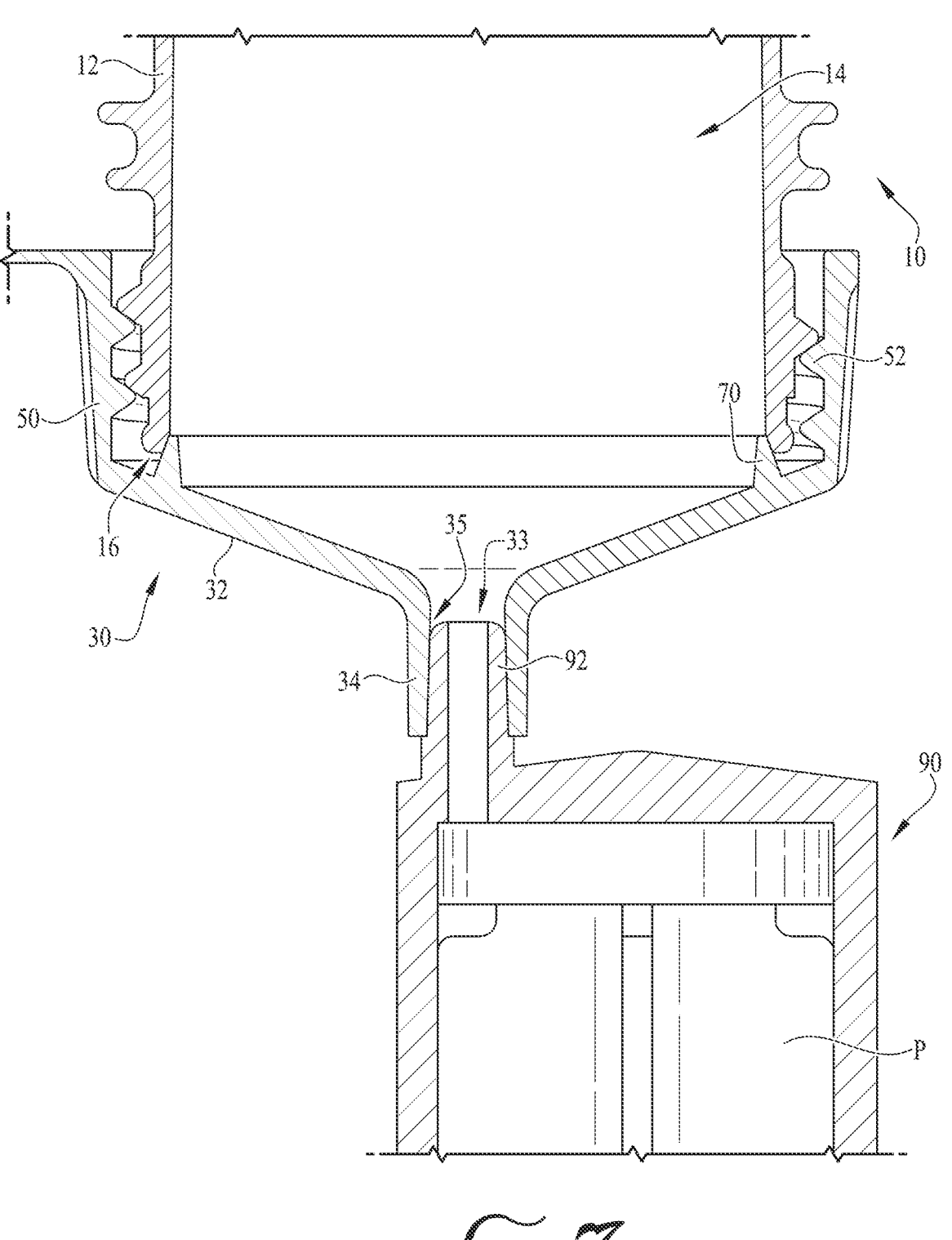
_Fig.7_

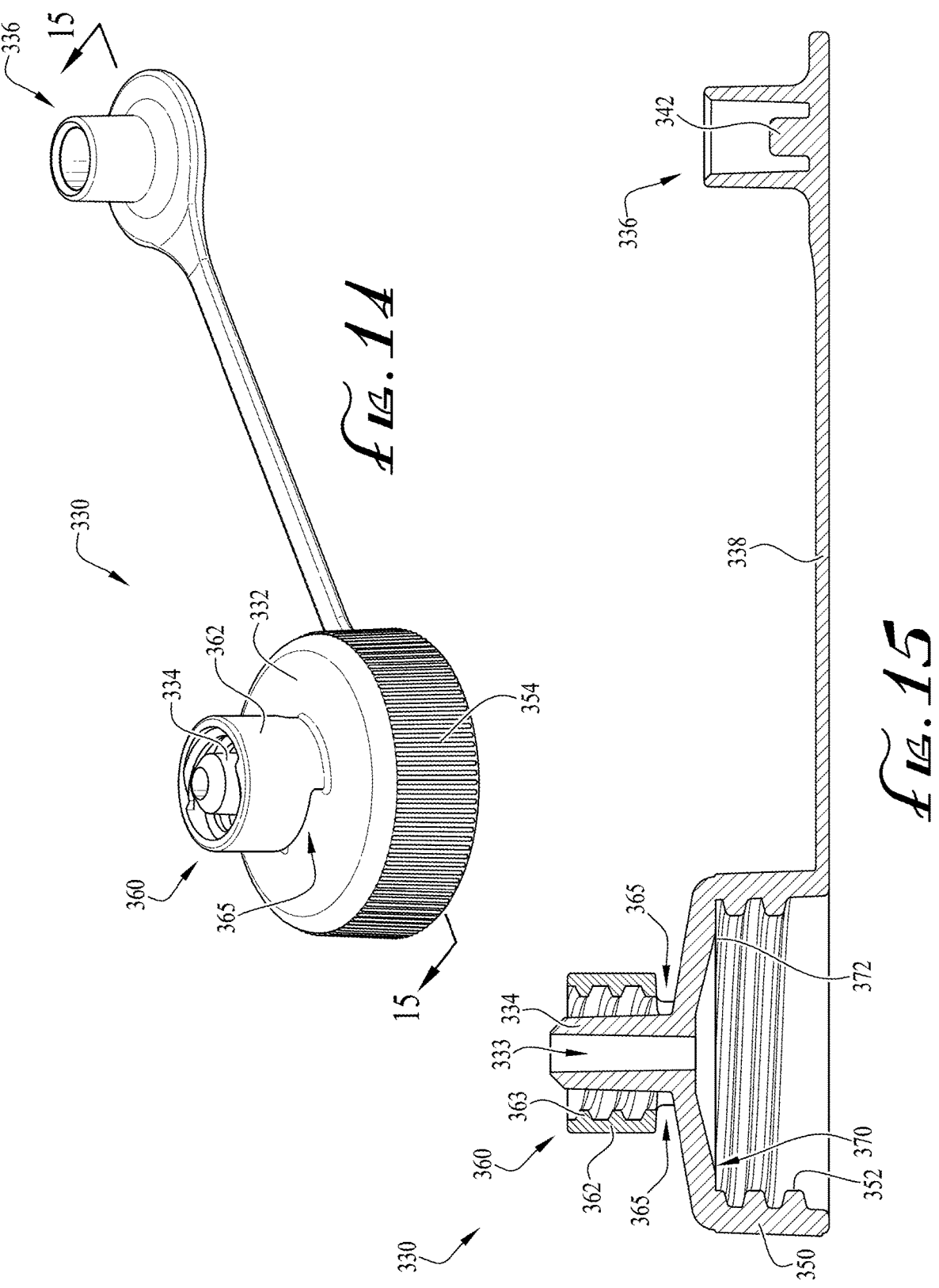

VENTED FLUID TRANSFER LID

CROSS-REFERENCE TO RELATED APPLICATIONS

This application is a continuation of U.S. patent application Ser. No. 15/782,695 filed Oct. 12, 2017, which claims the priority benefit of U.S. Provisional Patent Application Ser. No. 62/407,140 filed Oct. 12, 2016 and U.S. Provisional Patent Application Ser. No. 62/516,908 filed Jun. 8, 2017, the entireties of which are hereby incorporated herein by reference for all purposes.

TECHNICAL FIELD

The present invention relates generally to the field of containment, storage and delivery of fluids, and more particularly to a transfer lid for an enteral fluid container such as a bottle or breast pump collection container providing vented transfer of fluids such as formula or breast milk to or from the container.

BACKGROUND

Various containers are used for collection, storage and delivery of enteral fluids such as breast milk, formula, medications, supplements and the like. For example, breast milk may be collected in a collection container of a breast pump, transferred to a storage container for storage, and/or transferred to a bottle or syringe for feeding an infant, for example, orally via a bottle nipple or enterally via a feeding tube or line.

Maintaining sanitary and aseptic conditions in the handling of such enteral fluids is desirable. Various fluid collection, storage and delivery container systems have been developed. For example, U.S. Pat. No. 9,433,562, which is incorporated herein by reference, shows an example system for aseptic collection and enteral delivery of fluids. In some instances, a transfer lid is provided for attachment to the storage container, for example, to facilitate the transfer of fluid to and out of the storage container. U.S. Pat. No. 11,027,901, which is incorporated herein by reference, shows an example transfer lid having an inner collar including a vent slot allowing airflow therethrough, for example, to accommodate normal rates of transfer of the contained fluid. According to some example embodiments, enteral syringes and other components have enteral couplings conforming to the new ISO 80369-3 design standard (commonly known as ENFIT). U.S. Pat. No. 9,926,185, which is incorporated herein by reference, show example transfer lids having couplings that are formatted according to the new ISO 80369-3 design standard.

Continued improvements to collection, storage and delivery containers and systems are sought. It is to the provision of an improved transfer lid for such containers, and to containment systems incorporating such a transfer lid that the present invention is primarily directed.

SUMMARY

In example embodiments, the present invention provides a transfer lid having at least one vent path for permitting air to pass through at least one engagement interface or seal provided between the transfer lid and a container removably coupled to the transfer lid.

In one aspect, the present invention relates to a vented transfer lid for coupling engagement with an open threaded end of a container, the vented transfer lid includes a generally circular top panel having a transfer port extending from a generally central position on the top panel outwardly in a first or distal direction. An attachment collar extends in a second or proximal direction from the top panel, and an interior circumferential face of the attachment collar includes threads for releasable engagement with corresponding exterior threads of the open threaded end of the container. An inner collar projects from the top panel of the transfer lid in the second or proximal direction, with the inner collar being generally concentric with and spaced a distance inwardly from the attachment collar, and including an outer circumferential surface having a texturized electrical discharge machining (EDM) surface finish.

In example embodiments, the open threaded end of the container includes an inner surface configured for interengagement with the texturized EDM surface finish of the outer circumferential surface. In example embodiments, the inner surface of the open threaded end is substantially smooth. Optionally, the inner surface of the open threaded end comprises a texturized EDM surface finish. In example embodiments, the EDM surface finish generally comprises a Verein Deutsher Ingenieure (VDI) 3400 standard range of between about 24-42.

In another aspect, the invention relates to a transfer lid for coupling engagement with an open threaded end of a container. The transfer lid includes a generally circular top panel having a transfer port extending from a generally central position on the top panel outwardly in a first or distal direction, and an attachment collar extending in a second or proximal direction from the top panel, wherein an interior circumferential face of the attachment collar includes threads for releasable engagement with corresponding exterior threads of the open threaded end of the container. In example embodiments, at least a portion of an interior surface of the top panel includes a texturized EDM surface finish, and wherein the open threaded end of the container removably couples to the attachment collar such that a vent path is provided between the texturized EDM surface finish of the interior surface of the top panel and the open threaded end of the container.

In still another aspect, the invention relates to a transfer lid for coupling engagement with an open threaded end of a container, and for facilitating the transfer of fluids between the container and a syringe comprising a male connector. The transfer lid includes a generally circular top panel having a transfer port extending from a generally central position on the top panel outwardly in a first or distal direction, and an attachment collar extending in a second or proximal direction from the top panel, wherein an interior circumferential face of the attachment collar includes threads for releasable engagement with corresponding exterior threads of the open threaded end of the container. In example embodiments, at least a portion of an interior surface of the transfer port includes a texturized EDM surface finish. In example embodiments, with the attachment collar removably coupled to the open threaded end of the container, engagement of the male connector of the syringe with the interior surface of the transfer port provides a vent path such that air is permitted to flow within and out of the container, through the vent path during the transfer of fluids between the container and the syringe. In example embodiments, at least a portion of the lid comprises an outer layer exhibiting oleophobic or hydrophobic characteristics.

In yet another aspect, the invention relates to a transfer lid for coupling engagement with an open threaded end of a container including a top panel and an attachment collar. The top panel includes a transfer port extending from a generally central position on the top panel outwardly in a first or distal direction, wherein the transfer port is configured for compatible engagement with a coupling of a syringe. The attachment collar extends in a second or proximal direction from the top panel, wherein an interior circumferential face of the attachment collar includes threads for releasable engagement with corresponding exterior threads of the open threaded end of the container. In example embodiments, at least a portion of the transfer port includes a texturized surface finish, and wherein engagement of the coupling of the syringe with the transfer port defines an engagement interface comprising at least one vent path.

In example embodiments, the transfer port includes a female enteral-only coupling and the coupling of the syringe comprises a male enteral-only coupling. In example embodiments, the transfer port includes a male ISO 80369-3 formatted coupling and the coupling of the syringe includes a female ISO 80369-3 formatted coupling. In example embodiments, the texturized surface finish is applied to at least a portion of an inner surface of the top panel.

In yet another aspect, the invention relates to a transfer lid for coupling engagement with an open threaded end of a container including a top panel and an attachment collar. The top panel includes a transfer port extending from a generally central position on the top panel outwardly in a first or distal direction, wherein the transfer port is configured for compatible engagement with a coupling of a syringe. The attachment collar extends in a second or proximal direction from the top panel, wherein an interior circumferential face of the attachment collar includes threads for releasable engagement with corresponding exterior threads of the open threaded end of the container. In example embodiments, at least a portion of an interior surface of the top panel includes a texturized surface finish, and wherein the open threaded end of the container removably couples to the attachment collar such that at least one vent path is provided between the texturized surface finish of the interior surface of the top panel and the open threaded end of the container.

In example embodiments, the transfer port includes a female enteral-only coupling and the coupling of the syringe comprises a male enteral-only coupling. In example embodiments, the transfer port includes a male ISO 80369-3 formatted coupling and the coupling of the syringe includes a female ISO 80369-3 formatted coupling.

In yet another aspect, the invention relates to a fluid transfer lid for removably coupling a container with a syringe, wherein fluids can be transferred therebetween, wherein an engagement interface is defined between the connection of the fluid transfer lid and the container and the connection of the fluid transfer lid and the syringe, and wherein at least one of the engagement interfaces is configured such that at least one vent path is provided to permit air ventilation but prevent liquids from passing therethrough.

These and other aspects, features and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description of example embodiments are explanatory of example embodiments of the invention, and are not restrictive of the invention, as claimed.

BRIEF DESCRIPTION OF THE DRAWINGS

FIG. 4 is a close-up cross-sectional view of the engagement of the seal of the vented fluid transfer lid with an end surface of the open threaded end of the bottle according to an example embodiment of the present invention.

FIG. 5 is a close-up cross-sectional view of the engagement of the seal of the vented fluid transfer lid with an end surface of the open threaded end of the bottle according to another example embodiment of the present invention.

FIG. 6 is a close-up cross-sectional view of the engagement of the seal of the vented fluid transfer lid with an end surface of the open threaded end of the bottle according to another example embodiment of the present invention.

FIG. 7 shows a detailed view of the vented fluid transfer lid connected with the bottle and having the syringe connected to the fluid transfer port of FIG. 1, and showing the assembly thereof inverted to facilitate the transfer of fluids and allow venting according to another example embodiment of the present invention.

FIG. 14 is a vented fluid transfer lid according to another example embodiment of the present invention.

FIG. 15 is a cross-sectional view of the vented fluid transfer lid of FIG. 14 taken along line 15-15.

DETAILED DESCRIPTION OF EXAMPLE EMBODIMENTS

The present invention may be understood more readily by reference to the following detailed description of example embodiments taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

Example embodiments of the present invention relate to components for facilitating the transfer of fluids between separate containers or storage and delivery devices. In example embodiments, the containers as described herein can be a breast milk pump collection container, a feeding bottle for preparation and delivery of formula to an infant, a storage container for enteral fluids such as formula or milk, a pharmacy bottle for fluid medicine, or any of a variety of other container formats. The delivery devices can be in the form of a syringe or other fluid delivery device. Preferably, as will be described herein, the present invention relates to facilitating the transfer of fluids between the container and syringe, for example, wherein air is capable of being vented to or from a contained volume of the container, for example, as fluid is delivered into or out of the container through a transfer port of a vented fluid transfer lid.

As used herein, the term "VDI" refers to the Verein Deutscher Ingenieure 3400 Standard as of the date of priority of the application (i.e., Oct. 12, 2016). As used herein, the term "ISO 80369-3" refers to the ISO 80369-3 standard as of the date of priority of the application (i.e., Oct. 12, 2016).

Figure 1:
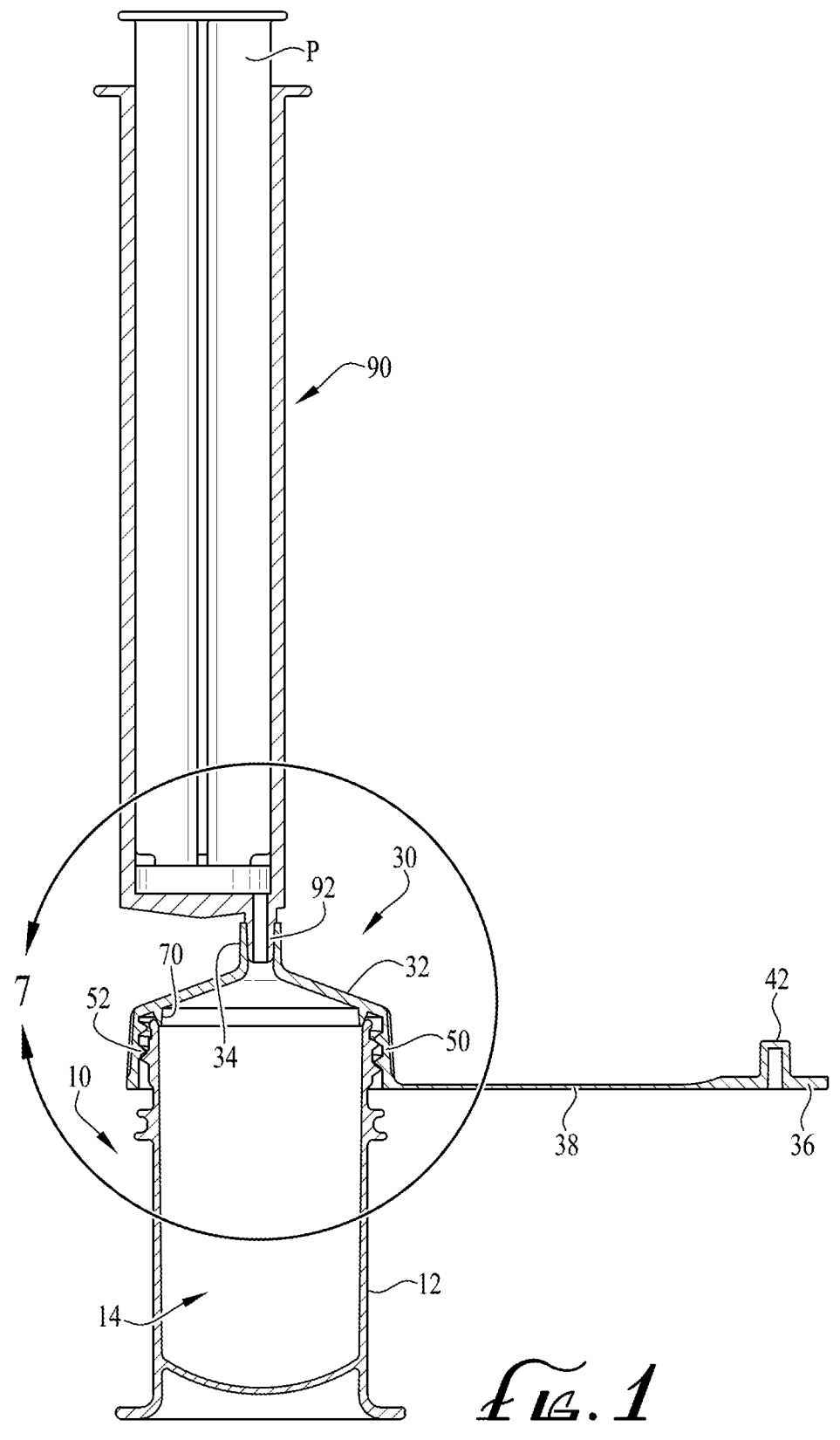
FIG. 1 is a cross-sectional view of a vented fluid transfer lid according to an example embodiment of the present invention, and showing a threaded collar of the vented fluid transfer lid connected to a bottle and a syringe connected to a transfer port thereof.
Figure 2:
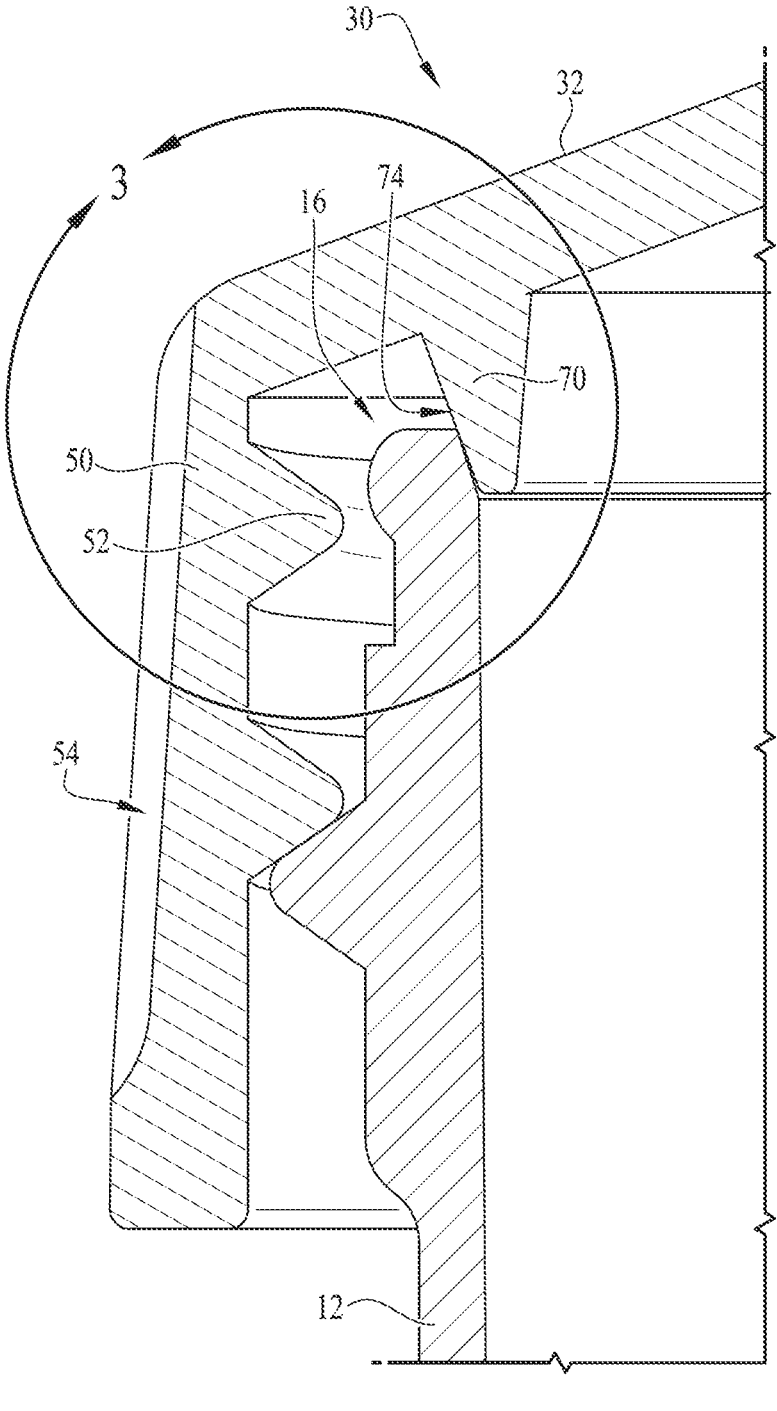
FIG. 2 is a detailed cross-sectional view of a portion of the connection of the threaded collar of the vented fluid transfer lid with the open threaded end of the bottle.
Figure 3:
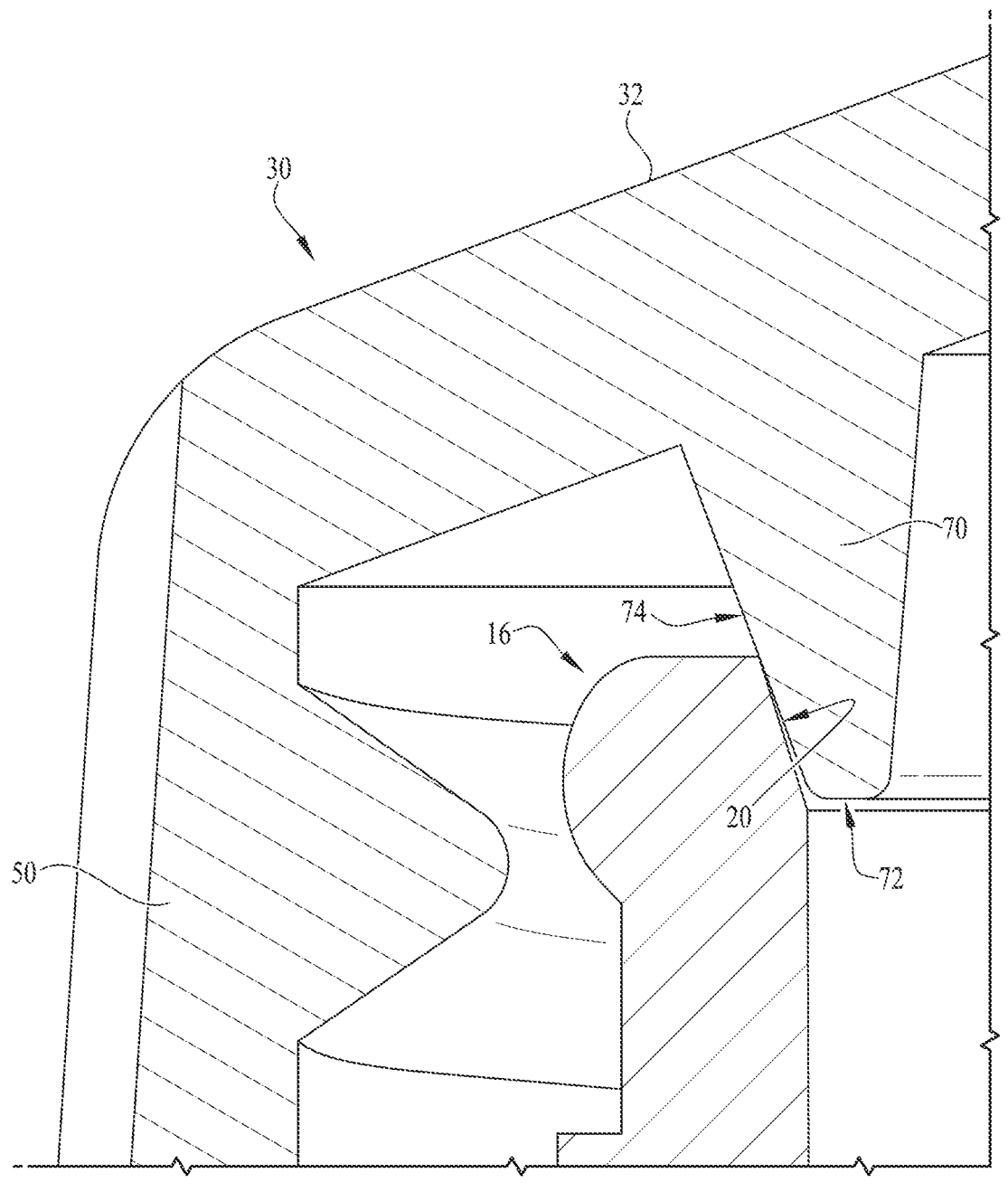
FIG. 3 is a close-up cutaway view of the connection of FIG. 2.

With reference now to the drawing figures, wherein like reference numbers represent corresponding parts throughout the several views, FIGS. 1-3 show a container 10 comprising a containment shell 12 and a threaded open upper end 16, to which a vented transfer lid or cap 30 is removably mounted to enable controlled venting, for example, wherein air is permitted to pass through a seal or engagement interface formed by the removable engagement or connection of the threaded open upper end 16 with the vented transfer lid 30.

In example embodiments, the container 10 comprises the containment shell 12, which encloses a contained volume 14 for the containment of fluids. In example embodiments, the container 10 is a breast milk pump collection container, a feeding bottle for preparation and delivery of formula to an infant, a storage container for enteral fluids such as formula or milk, a pharmacy bottle for storing medication, or any of a variety of other container formats. The containment shell 12 includes the threaded open upper end 16, to which the transfer lid 30 is removably mounted to enable selective opening and closing of the container for delivery of fluids to and from the contained volume 14. The threaded open upper end 16 including container threads, and a container sealing lip defining an outwardly extending rounded surface, a shoulder positioned between the container threads and the outwardly extending rounded surface, and an angled inner container surface radially inward of the outwardly extending rounded surface.

In example embodiments, the transfer lid 30 comprises a generally circular top panel 32 with a transfer port 34 (defining a conduit or lumen 33 extending therethrough) extending from a generally central position on the top panel outwardly in a first or distal direction. Optionally, a port closure cap 36 is attached to the transfer lid 30 by a tether 38, and includes a cover or plug 42 for removable engagement and closure of the transfer port 34 (and lumen 33 thereof). The transfer lid 30 further comprises an attachment collar 50 extending in a second or proximal direction from the top panel 32. In example forms, the transfer port 34 comprises an enteral-only (EO) coupling, for example an EO female coupling for releasable sealing engagement with a male EO coupling 92 of a transfer syringe 90 for transferring enteral fluids to and/or from the container 10. In example embodiments, the EO female coupling comprises a substantially smooth-surfaced interior cavity for receiving the male EO coupling of the transfer syringe, and thus, the interengagement therebetween provides for an air-tight seal. Optionally, the transfer port 34 comprises a self-sealing closure to allow fluid passage to or from a syringe inserted therein, but to prevent fluid leakage from the container and provide an air-tight seal forming an aseptic closure to prevent contamination from entering the container when the syringe is removed. Optionally, the sealing closure of the transfer port provides a positive sealing engagement with the cooperating coupling element of a transfer syringe, to prevent airflow, fluid leakage or potential transfer of contamination therebetween into or from the container. In further example embodiments, as will be described below, the transfer port 34 is optionally an enteral-only coupling compatible with the ENFIT design standard (ISO 80369-3). Thus, according to example embodiments, the transfer port comprises an ENFIT formatted coupling.

The interior circumferential face of the attachment collar 50 of the transfer lid 30 is threaded to releasably engage corresponding exterior threads at the top of the containment shell 12 near the rim around its open upper end 16. The threads 52 and attachment collar 50 are optionally configured for engagement with the threads of a containment shell compatible with the threaded connection hub of a standard breast pump. Various collar and thread configurations may be provided within the scope of the invention, for compatibility with different breast pump and/or other product designs and different manufacturer specifications. The exterior circumferential face of the attachment collar 50 of the transfer lid 30 optionally comprises spaced recesses, ridges or other gripping features 54 to assist a user in installing and removing the transfer lid onto and from the open upper end 16 of the containment shell 12. According to one example embodiment, the gripping features 54 defined a plurality of rib-like projections or indentions formed along the outer periphery of the attachment collar. In this manner, the containment shell 12 can be attached to a breast pump for collection of breast milk, then removed from the pump and the transfer lid 30 attached to the containment shell 12 to close the container 10 for storage or dispensing of the milk. Alternatively, the transfer lid 30 can be removed from the container 10 to allow artificial formula, supplements or other fluids to be prepared through the open top of the containment shell, and the transfer lid replaced for storage and dispensing.

A circumferential sealing flange or inner collar 70 projects from the top panel 32 of the transfer lid 30 in the second or proximal direction, generally concentric with and spaced a distance inwardly from the attachment collar 50. In example embodiments, at least a portion of the inner collar 70 comprises a diameter that is less than the inside diameter of the attachment collar 50 by a dimension selected to define a spacing between the attachment collar 50 and the inner collar 70 corresponding to the material thickness of the containment shell 12 around its upper rim or threaded open upper end 16. In this manner, when the transfer lid 30 is attached to the containment shell 12, the open upper end 16 of the containment shell 12 is engaged between the inner circumferential face of the attachment collar 50 on the outside of the containment shell, and an outer circumferential face 74 of the inner collar 70 on the inside of the containment shell, with a generally close fit therebetween.

As depicted in FIG. 3, a free end 72 of the inner collar 70 opposite its attachment to an interior surface of the top panel 32 generally comprises a radiused or tapered profile to provide an interface as the rim of the containment shell 12 (or threaded open upper end 16) passes along the inner collar 70 during installation and removal of the transfer lid 30 with the container 10. According to one example embodiment, the material of the inner collar 70 is sufficiently thin and resilient to allow a degree of flexure or inward compression upon contact with the rim of the containment shell 12 for easier installation and removal of the transfer lid 30. For example, in example embodiments, the inner collar 70 in its relaxed, non-flexed state is dimensioned to at least partially interfere with the threaded open upper end 16. Thus, the inner collar 70 is generally dimensioned to provide at least some interference to provide for fitting engagement with an inner surface 20 of the threaded open upper end 16. In example embodiments, it is the engagement between the inner surface 20 of the threaded open upper end 16 of the container 10 and the outer circumferential surface 74 of the inner collar 70 which provides an engagement interface sufficient for preventing liquids from passing therethrough, but permits air to vent (as will be described below).

As depicted in FIGS. 1-3, with the transfer lid 30 removably engaged with the threaded open upper end 16 of the container 10, the inner surface 20 of the threaded open upper end 16 engages with at least a portion of the outer circumferential surface 74 of the inner collar 70, thereby defining the engagement interface which permits venting of air (as will be described below). In example embodiments, at least a portion of outer circumferential surface 74 of the inner collar 70 comprises a texturized surface, which when engaged with the upper inner surface 20 of the container 10, preferably provides a liquid-tight seal, for example, wherein a plurality of micro ventilation channels or conduit web(s) allow for air to be vented (e.g., permitting air to pass through the micro vent channels or web(s)) but prevent liquids from passing therethrough.

Thus, for example, when the transfer lid 30 is removably engaged with the threaded open upper end 16 of the container 10 and the upper inner surface 20 of the container 10 is engaged with at least a portion of the outer circumferential surface 74 of the inner collar 70 (defining the engagement interface), fluid within the container can be transferred through the transfer lid (via the transfer port 34 of the transfer lid 30) to a syringe 90 while allowing air ventilation, for example, permitting air to pass through the engagement interface from the atmosphere exterior of the container 10 and transfer lid 30 to within the contained volume 14 of the containment shell 12 of the container 10. In a similar manner, fluids within the syringe 90 can be transferred through the transfer port 34 of the transfer lid 30 and into the container 10 while allowing air ventilation. In example embodiments, with at least a portion of the outer circumferential surface 74 of the inner collar 70 being texturized, air is permitted to vent and be drawn within or released from the contained volume 14 of the container 10, for example as fluid is delivered into or out of the container through the transfer port 34 of the transfer lid 30.

For example, whether transferring fluids from the syringe 90 to the container 10, or vise-versa with fluids being transferred from the container 10 to the syringe 90, the texturized outer circumferential surface 74 of the inner collar 70 permits an equalization or exchange of fluids, for example, so that the contained volume 14 of the container 10 does not become pressurized (e.g., positive or negative pressure). For example, with the containment volume 14 of the container 10 being substantially empty and without fluids therein (e.g., generally only air being present therein), the introduction of fluids within the contained volume 14 (from the syringe 90 and through the transfer port 34 of the transfer lid 30) causes the air within the contained volume 14 to become pressurized. However, by providing an engagement interface between the container 10 and the transfer lid 30 (e.g., wherein at least a portion thereof comprises a texturized surface), a given quantity or volume of fluid transferred within the contained volume 14 likewise permits a similar quantity or volume of air within the containment volume 14 to be vented or pass through the engagement interface into the atmosphere, thereby equalizing the pressure within the contained volume.

In example embodiments, the outer circumferential surface 74 can be texturized as desired, for example, generally comprising a desired EDM surface finish. According to one example embodiment, the EDM surface finish of the outer circumferential surface 74 is generally between a VDI range of about 12-45, more preferably between about 24-42. For example, according to one example embodiment, the EDM surface finish of the outer circumferential surface 74 comprises a VDI range of between about 27-30, for example when at least some venting is desired. In another example embodiment, the EDM surface finish of the outer circumferential surface 74 comprises a VDI range of about 33. Optionally, the VDI value associated with the EDM surface finish can be chosen as desired. According to example embodiments, the inner surface 20 of the threaded open upper end 16 comprises a substantially smooth surface finish for providing engagement with the texturized outer circumferential surface 74 of the inner collar 70. In alternate embodiments, the inner surface 20 comprises a texturized EDM surface finish and the outer circumferential surface 74 of the inner collar 70 is substantially smooth. Optionally, both the inner surface 20 and the outer circumferential surface 74 comprise a texturized EDM surface.

In example embodiments, the texturized EDM surface finish is provided by electrical discharge machining (EDM), for example, wherein the mold, cavity or tool used to mold one or more components or transfer lids as described herein is provided with the desirable EDM surface finish. Thus, any components or transfer lids molded by the tool or mold comprise the EDM surface finish thereon. In example embodiments, the EDM surface finish can be substantially smooth (e.g., exhibiting a substantially small amount of texture) or can be substantially rough (e.g., exhibiting a substantial amount of texture). In example embodiments, a surface finish standard, for example, the Verein Deutsher Ingenieure (VDI) 3400 standard, can be used to associate the EDM surface finish with a value. For example, the VDI 3400 standard includes values between 0-45, wherein a VDI value of 0 is substantially smooth with a marginal amount of texture, and wherein a VDI value of 45 is substantially rough with a substantial amount of texture or roughness. As described above, the outer circumferential surface 74 comprises an EDM surface finish having a VDI value of between about 12-45. Optionally, as will be described herein, the VDI value of the EDM surface finish can be chosen as desired. Furthermore, as described below, other methods of forming a texturized surface finish can be provided, for example, by chemical etching, sandblasting, or other surface texturizing methods.

As depicted in FIGS. 4-6, the engagement interface that is defined by the engagement of the inner collar 70 with the inner surface 20 of the threaded open upper end 16 can be configured as desired. For example, as depicted in FIGS. 4-5, an angle α can be defined between the outer circumferential surface 74 of the inner collar 70 and the inner surface 20 of the threaded open upper end 16 of the container 10, for example, wherein with the transfer lid 30 being removably engaged with the threaded open upper end 16, the outer circumferential surface 74 is oriented at an angle α relative to the inner surface 20. According to another example embodiment, the inner surface 20 and the outer circumferential surface 74 are generally parallel with respect to each other, for example, wherein a majority of each of the surfaces thereof are generally engaging or in contact with each other (see FIG. 6). Typically, the inner surface 20 and the outer circumferential surface 74 are generally planar and angled such that engagement therebetween provides a substantially close-fitting engagement of the surfaces (e.g., the engagement interface). However, in alternate embodiments, one or both of the surfaces can be radiused or otherwise shaped as desired for providing a desirable amount of contact or interference therebetween. Preferably, the amount of contact or interference of the two surfaces (inner surface 20 and outer circumferential surface 74) determines the rate at which air can vent or pass through the engagement interface. For example, the engagement interface as shown in FIGS. 4-5 generally allows for a greater amount of air ventilation as compared to the engagement interface of FIG. 6. According to some example embodiments, the inner surface 20 and/or outer circumferential surface 74 of the inner collar 70 comprises a substantially uniform indention, protrusion, or other surface feature to facilitate the engagement therebetween, for example, wherein one or more of the surfaces defining the engagement interface therebetween comprises a texturized surface.

As described above and according to some example embodiments, the transfer port 34 comprises an enteral-only (EO) coupling, for example a female EO coupling for releasable sealing engagement with the male EO coupling 92 of the transfer syringe 90 for transferring enteral fluids to and/or from the container 10. According to one example embodiment, the female EO coupling of transfer port 34 comprises a substantially smooth-surfaced interior cavity for receiving the substantially smooth-surfaced male EO coupling of the transfer syringe, and thus, the interengagement therebetween provides for an air-tight seal. Thus, when an air-tight seal is provided between the engagement of the female EO coupling of transfer port 34 and the male EO coupling 92, the engagement interface between the inner surface 20 of the threaded open upper end 16 and the texturized outer circumferential surface 74 preferably provides for at least some ventilation therebetween, for example, to permit air to pass therethrough but prevent any liquids from passing therethrough. However, according to another example embodiment, at least a portion of the engagement of the female EO coupling of transfer port 34 with the male EO coupling 92 can be configured such that air is permitted to pass therebetween but prevent liquid from passing therebetween. For example, as depicted in FIG. 7, an interior surface 35 of the transfer port 34 can be at least partially texturized (or comprise any desirable texturized EDM surface treatment) such that one or more micro ventilation channels permit air to pass therethrough when the male EO coupling 92 is fully engaged with the female EO coupling of transfer port 34 of the transfer lid 30. In alternate embodiments, at least a portion of both the interior surface 35 of the transfer port 34 and an exterior surface of the coupling 92 comprise a texturized EDM surface treatment.

Figures 8, 9:
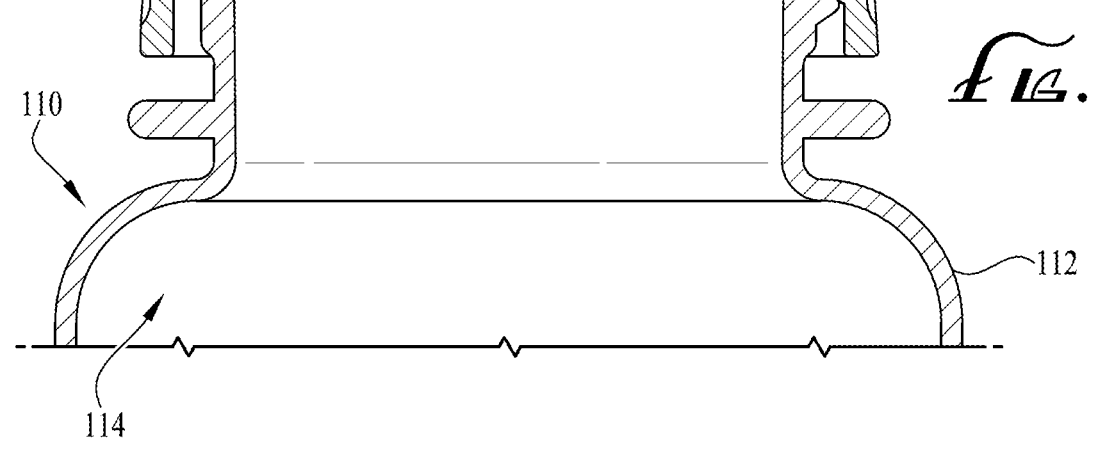
FIG. 8 shows a bottom plan view of a vented fluid transfer lid according to another example embodiment of the present invention.
FIG. 9 shows a cross-sectional view of the vented fluid transfer lid of FIG. 8, and showing the vented fluid transfer lid connected to an open threaded end of a bottle.
Figure 10:
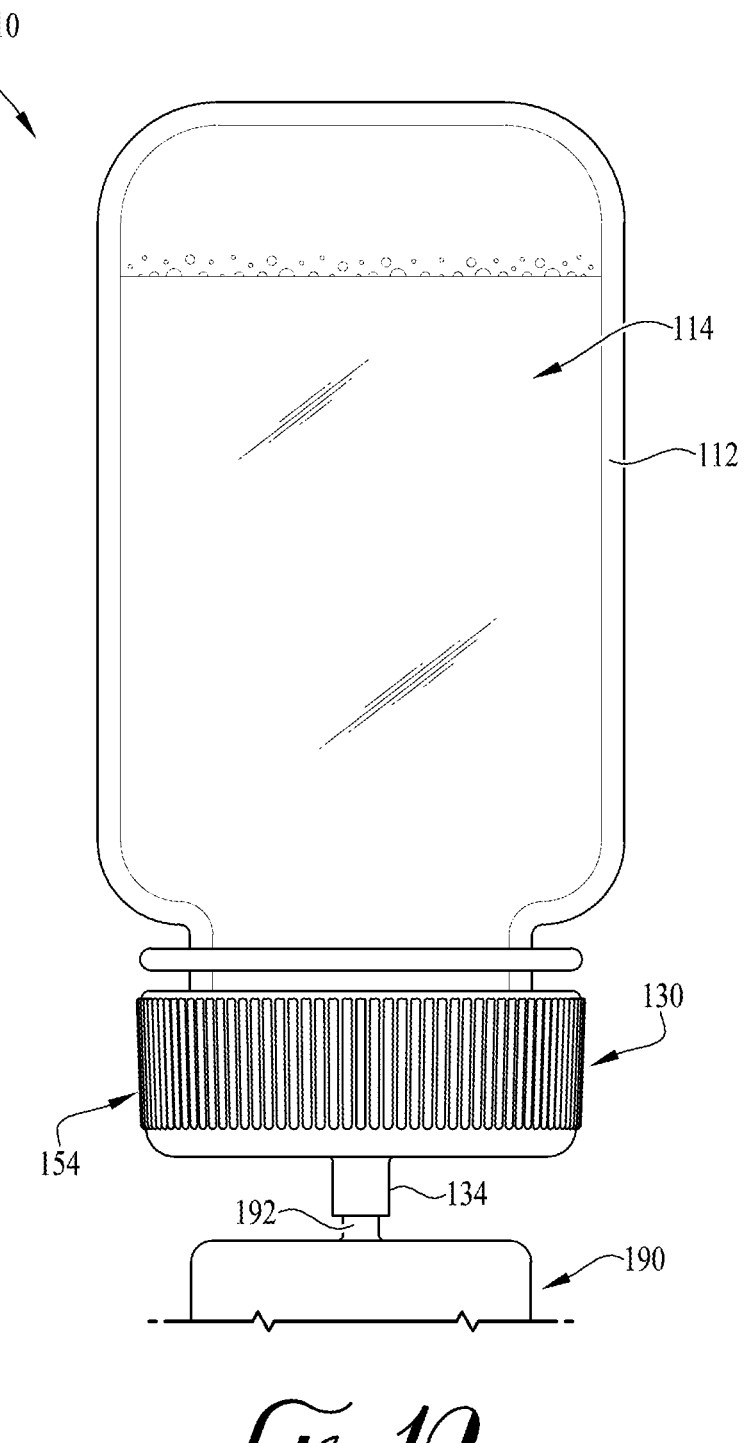
FIG. 10 shows the vented fluid transfer lid and bottle of FIG. 9, showing the bottle inverted to provide for facilitating the transfer of fluids between the syringe and the bottle.

FIGS. 8-10 show a transfer lid 130 according to another example embodiment. In example embodiments, the transfer lid 130 comprises an inner collar 170 having a texturized EDM surface 172 for engagement with a container 110, for example, for engagement with an threaded open upper end 116 of the container 110 to define an engagement interface therebetween. In example embodiments, the engagement interface defined between the texturized EDM surface 172 and the threaded open upper end 116 of the container 110 is configured as similarly described above, for example, such that a plurality of micro ventilation channels are defined at the engagement interface and permit the venting of air into and out of the container 110. As depicted in FIG. 10, with male EO coupling 192 of the syringe 190 fitted within the female EO coupling of transfer port 134 (or opening) of the transfer lid 130, the container 110 (having the transfer lid 130 attached thereto) is inverted (e.g., oriented upside down), and wherein the plunger P is retracted to withdraw or transfer fluids from the container 110 and into the barrel of the syringe 190.

Preferably, with the inner collar 170 having the texturized EDM surface 172 engaged with the threaded open upper end 116 of the container 110, air is permitted to pass through the engagement interface and prevent a vacuum from forming within the container, for example, when fluids are drawn from the container 110 to within the barrel of the syringe 190. Similarly, fluid from within the syringe barrel can be transferred to the container 110, for example, wherein the discharging of fluids from the syringe 190 to within the container by compression or actuation of the plunger P (causing fluids to pass through the transfer lid 130) allows for air that is within the container 110 to vent out of the container 110, for example, as the container 110 begins to be filled with the fluid. For example, as more fluid is transferred from the syringe 190 to within the container 110, a generally equivalent volumetric amount of air can be released or vented to the atmosphere (e.g., by passing through the engagement interface). Similarly, when transferring fluids from the container 110 to the syringe 190, any vacuum created in the container due to fluids transferring from the containment volume to the syringe can be relieved by permitting atmospheric air to pass through the vented engagement interface and within the container 110. In example embodiments, rather than the engagement interface being between the outer surface 74 of the inner collar 70 and an inner surface 20 of the threaded open upper end 16 (as depicted in FIGS. 1-7), the engagement interface of the transfer lid 130 and the container 110 is such that an outer periphery or end portion of the threaded open upper end 116 of the container 110 engages with the texturized EDM surface 172 of the inner collar 170. Thus, the texturized EDM surface 172 is defined about an interior circumferential portion of the inner collar 170, for example, rather than an outer circumferential portion as shown in the transfer lid 30. In alternate embodiments, the texturized EDM surface 172 can be on an outer circumferential surface of the inner collar 170 for engagement with an inner end surface of the threaded open upper end 116 of the container 110, thereby defining a vented engagement interface such that air is permitted to pass therethrough, but wherein liquids are prevented from passing therethrough.

Optionally, according to another example embodiment and as similarly described above, at least a portion of the interior surface 135 of the transfer port 134 comprises a texturized EDM surface finish, for example, such that when the transfer port 134 is engaged with the male EO coupling 192 of the syringe 190, at least one micro vent channel is provided at the engagement interface such that air is permitted to pass therethrough during the transfer of fluids from the container 110 to the syringe 190, or for example, from the syringe 190 to the container 110. The embodiment illustrated in FIGS. 8-10 includes elements similar to the embodiment illustrated in FIGS. 1-7, for example: the container 110 comprises a containment shell 112, which encloses a contained volume 114 for the containment of fluids; the transfer lid 130 comprises a generally circular top panel 132 with the female EO coupling 134 (defining a conduit or lumen 133 extending therethrough); and the transfer lid 130 further comprises an attachment collar 150 and gripping features 154.

Figure 11:
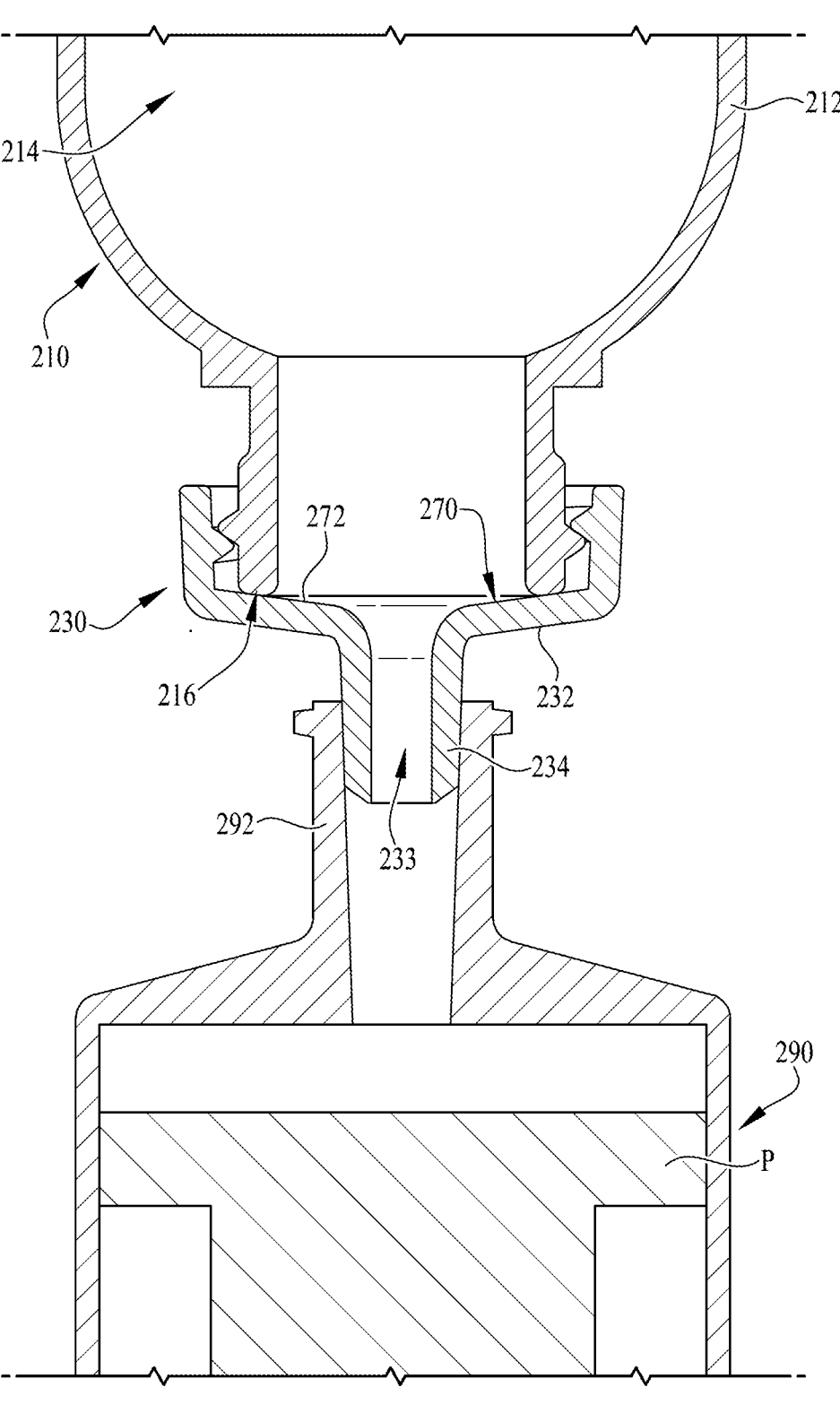
FIG. 11 shows a cross-sectional view of a vented fluid transfer lid according to another example embodiment of the present invention, and showing the vented fluid transfer lid connected to an open threaded end of a bottle and a syringe connected to the fluid transfer port of the vented fluid transfer lid.
Figure 12:
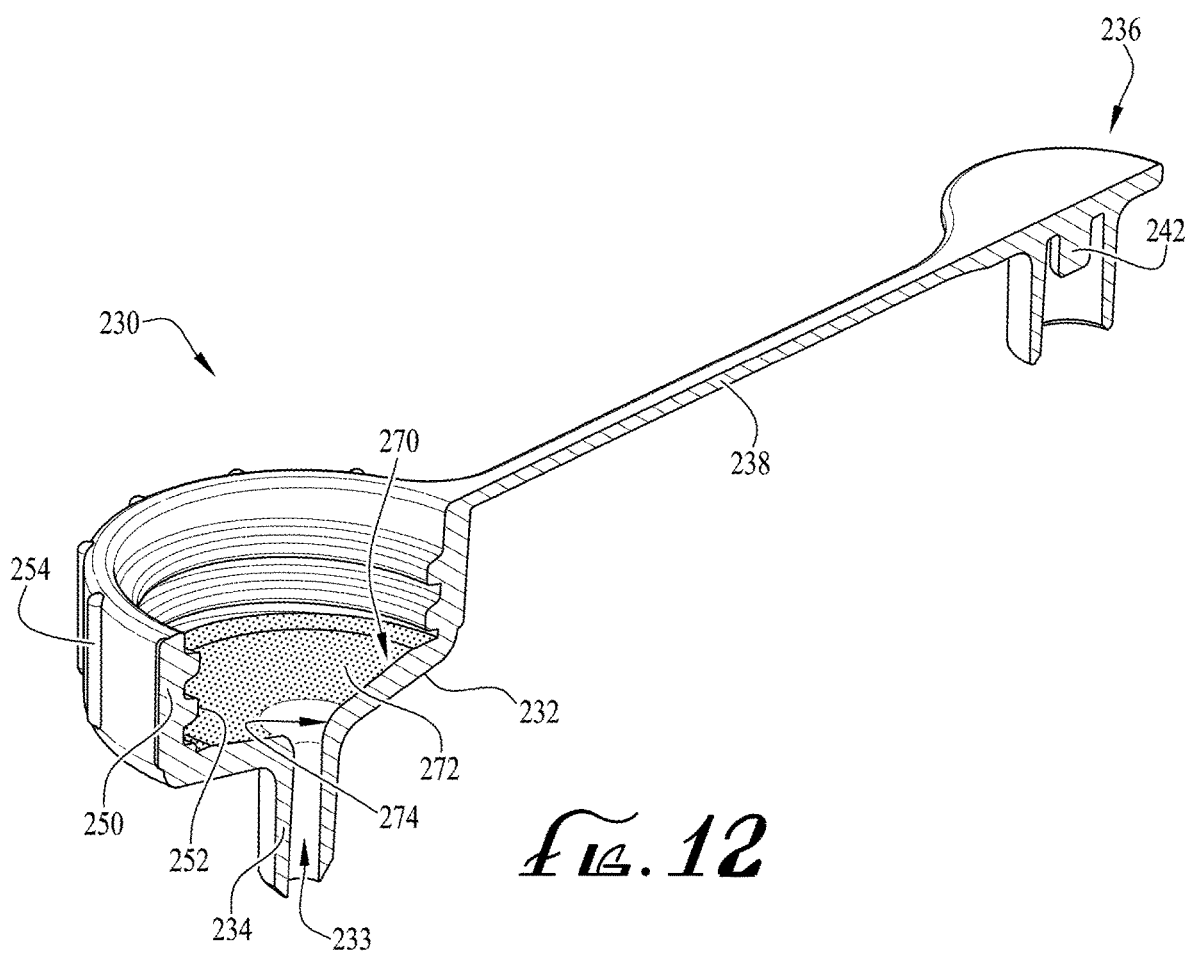
FIG. 12 is a perspective cross-sectional view of the vented fluid transfer lid of FIG. 11.
Figure 13:
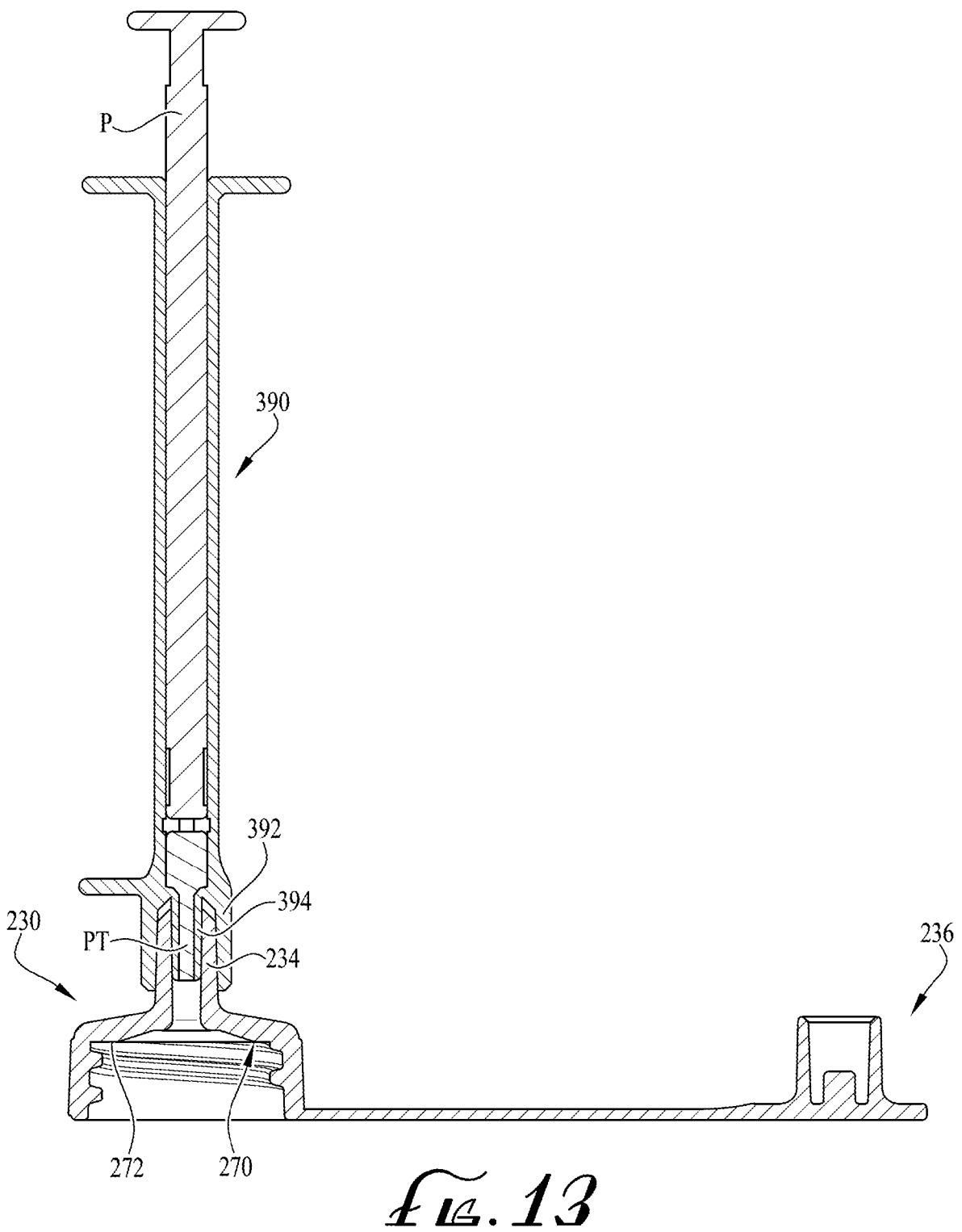
FIG. 13 is a cross-sectional view of the vented fluid transfer lid of FIG. 12, showing a syringe having a lumen extension tip connected with the fluid transfer port of the vented fluid transfer lid.

FIGS. 11-13 show a transfer lid 230 according to another example embodiment of the present invention. In example embodiments, the transfer lid 230 is connected to an threaded open upper end 216 of a container 210 and a syringe 290 is connected to a transfer port 234 of the transfer lid 230 such that fluids can be transferred between the container 210 and the syringe 290, for example, wherein an engagement interface defined between the transfer lid 230 and the threaded open upper end 216 of the container define at least one or more micro ventilation channels, conduit web(s), or vent paths provide for air ventilation but prevent liquids from passing therethrough. The embodiment illustrated in FIGS. 11-13 includes elements similar to the embodiment illustrated in FIGS. 1-7, for example: the container 210 comprises a containment shell 212, which encloses a contained volume 214 for the containment of fluids.

In example embodiments, the transfer lid 230 is generally similar to the transfer lids 30, 130 as described above, for example, comprising a top panel 232 with a transfer port 234 (defining a lumen 233 extending therethrough) extending from a generally central position on the top panel outwardly in a first or distal direction (see FIG. 12). Optionally, a port closure cap 236 is attached to the transfer lid 230 by a tether 238, and includes a cover or plug 242 for removable engagement and closure of the transfer port 234 (and lumen 233 thereof). The transfer lid 230 further comprises an attachment collar 250 (comprising one or more internal threads 252) extending in a second or proximal direction from the top panel 232 for removable engagement with the threaded open upper end 216 of the container 210. At least a portion of an inner surface 270 (generally opposite the top panel 232) comprises a texturized EDM surface finish 272 such that the engagement interface (e.g., defined by engagement of the threaded open upper end 216 with the EDM surface finish 272 of the inner surface 270) provides one or more micro ventilation channels or vent paths for permitting air to vent or pass through the engagement interface but prevent liquids from passing therethrough. In example embodiments, the inner surface 270 is generally sloped (at least slightly) towards the lumen 233 of the transfer port 234. In alternate example embodiments, the inner surface 270 is generally planar or can be otherwise sloped as desired.

In example embodiments, the entirety of the inner surface 270 can comprise the texturized EDM surface finish 272. In alternate embodiments, only one or more portions of the inner surface 270 can comprise the texturized EDM surface finish, for example, wherein a portion of the inner surface 270 that is generally in contact with the threaded open upper end 216 comprises the texturized EDM surface finish 272, and wherein other portions of the inner surface 270 are generally smooth. For example, according to some example embodiments, the texturized EDM surface finish 272 is provided along a ring-shaped or circular path around the entire circumference of the inner surface 270 where the threaded open upper end 216 of the container 210 contacts the inner surface 270 to define the engagement interface. Optionally, a circular array of texturized EDM surface finish segments can be provided, for example, such that an alternating surface finish is provided (e.g., alternating between a texturized EDM surface segment and a substantially smooth surface segment). Further optional, both the inner surface 270 and the threaded open upper end 216 of the container 210 can comprise one or more portions having the texturized EDM surface finish.

In example embodiments, a radiused transition 274 is provided between the inner surface 270 and the lumen 233 of the transfer port 234, thereby forming a funnel-like shape on the interior of the transfer lid 230. In example embodiments, with the inner surface 270 being at least slightly sloped and with the radiused transition 274, fluid medicine or other fluids flow easier through the lumen 233 of the transfer port 234 and into the syringe 290. Thus, when considering fluid medicine, the radiused transition 274 preferably provides benefit to the medicine being transferred therethrough, for example, wherein the fluid medicine is not subjected to the amount of shear or other forces that are generally caused by interaction between the fluid and an interior of the lid. Thus, according to some example embodiments, the inner surface 270 and the radiused transition 274 provide a less agitated or disturbed transfer of fluids between the container 210 and the syringe 290.

In example embodiments, the transfer port 234 comprises an ISO 80369-3 formatted coupling, for example, a male ENFIT formatted coupling, and the syringe 290 comprises a coupling 292 that is a female ENFIT formatted coupling conforming to the ISO 80369-3 design standard. U.S. Pat. No. 9,926,185, which is incorporated herein by reference, shows example transfer lids having couplings that are formatted according to the ISO 80369-3 design standard. In alternate example embodiments, the transfer port 234 can comprise a female ENFIT formatted coupling and the syringe can comprise a male ENFIT formatted coupling. U.S. Pat. No. 10,682,287 is incorporated herein by reference in its entirety, and shows example transfer lids having transfer ports in the form of female ENFIT formatted couplings according to the ISO 80369-3 design standard.

As depicted in FIG. 13 and according to one example embodiment of the present invention, a syringe 390 comprising a coupling 392 and a dosing control coupling 394 can be provided for engagement with the transfer port 234 of the transfer lid 230. According to some example embodiments, the plunger P of the syringe 390 comprises an end tip portion PT that is configured to extend within the entirety of the lumen of the dosing control coupling 394. According to some example embodiments, as similarly described above, the outer surface of the transfer port 234 and/or an interior surface of the syringe coupling 292, 392 can comprise a texturized EDM surface finish to provide additional engagement interfaces where one or more vent paths permit air ventilation but prevent liquids from passing therethrough.

According to another example embodiment of the present invention, a fluid transfer lid 330 can comprise a cooperating connector 360 comprising an outer housing or collar 362 surrounding the transfer port 334, which extends outwardly in the first direction from the top panel 332. In example embodiments, the collar 362 comprises internal threads 363 for compatible engagement with one or more threads or lugs (see FIG. 11) formed on an outer surface of the syringe coupling 292, for example, such that a secure yet removable connection is provided between the syringe 290 and the transfer port 334. To provide for fluid drainage and airflow ventilation, a portion of the collar 362 optionally comprises at least one vent/fluid drainage opening 365 (depicted as two openings 365). U.S. Pat. No. 10,668,263 is incorporated herein by reference in its entirety, and shows an example connector comprising vent openings formed in the outer housing. As similarly described above, at least a portion of an inner surface 370 of the transfer lid 330 comprises a texturized EDM surface finish 372, for example, such that the engagement interface (when the open threaded end of the container is connected to the transfer lid) permits air ventilation but prevents liquids from passing therethrough. The embodiment illustrated in FIGS. 14-15 includes elements similar to the embodiment illustrated in FIGS. 1-7, for example: the fluid transfer lid 330 comprises the generally circular top panel 332 with the transfer port 334 (defining a conduit or lumen 333 extending therethrough); a port closure cap 336 is attached to the transfer lid 330 by a tether 338 and includes a cover or plug 342; and the transfer lid 330 further comprises an attachment collar 350 with threads 352.

In alternate embodiments, the vent/fluid drainage opening (s) are omitted, and a closed collar surrounds the transfer port 334. In alternate example embodiments, the collar 362 can comprise an array of clips, for example, a circular array of clips positioned around the transfer port 334 such that a dual action installation and removal mechanism is provided for engagement with the syringe coupling 292 (or threads or lugs thereof). The clips can provide for either removable or permanent engagement with the syringe coupling 292. U.S. Pat. No. 10,773,067 is incorporated herein by reference in its entirety and shows an example transfer lid having an array of clips provided around the transfer port to provide for a dual action installation and removal mechanism.

In example embodiments, the transfer lids 30, 130, 230, 330 of the present invention (and optionally transfer lids 430, 530 and 630 described below) preferably comprise at least a portion thereof having a texturized EDM surface finish, for example, which preferably allows for the passage of air through at least one seal or engagement interface provided between the transfer lid and the container, or for example, between the syringe port and the transfer lid. In example embodiments, one of the surfaces of the engagement interface (between the transfer lid and container or between the transfer lid and the syringe port) comprises the EDM surface finish, which when engaged or in sealing contact with the sealing surface provides a vent path or a plurality of micro air channels for permitting air to vent therethrough, but prevents fluids from flowing therethrough. In alternate example embodiments, both surfaces of the engagement interface (between the transfer lid and container and/or between the transfer port of the transfer lid and the syringe port) comprise the EDM surface finish, for example, to provide an alternate vent path configuration. In some example forms, when both surfaces of the engagement interface comprise the EDM surface finish, the VDI range values can be adjusted accordingly, for example, to provide an adequate vent path such that sufficient air venting is permitted.

In additional example embodiments, the texturized surface finishes as described herein can be configured as desired. For example, instead of the entire sealing surface of one or both of the surfaces of the engagement interface having a substantially uniform texturized surface finish, one or more of the surfaces can be segments of both texturized and generally smooth surfaces, for example, which can be sized, shaped and designed as desired. In example embodiments, one or more surfaces of the engagement interface can comprise a patterned texturized surface finish (e.g., lattice, checkered, directed channel(s), etc). Optionally, other texturized surface finish configurations can be chosen as desired.

According to another example embodiment of the present invention, one or more portions of the transfer lid, the container or other enteral couplings, connectors, fluid transfer members, syringes, etc. can comprise a hydrophobic or oleophibic coating or other surface treatment coating material(s) or layer(s) applied thereto. According to some example embodiments, a TEFLON, i.e., polytetrafluoroethylene (PFTE), coating is applied to at least a portion of the outer circumferential surface of the inner collar that comprises the texturized EDM surface finish. Optionally, other materials including TEFLON fluorinated ethylene propylene (FEP) fluoroplastic resin, TEFLON perfluoroalkoxy copolymer resin (PFA fluoroplastic resin), TEFLON (PTFE) fluoroplastic resin and/or TEFZEL ethylene-tetrafluoroethylene (ETFE) fluoroplastic resin can be used as desired. According to some example embodiments, prior to molding the transfer lid, the material used for forming the transfer lid is impregnated with the hydrophobic or oleophobic material. Optionally, one or more portions of the transfer lid can be co-molded with one or more hydrophobic or oleophobic materials. Optionally, the transfer lid can be sprayed with a hydrophobic or oleophobic coating, or for example, the transfer lid can be placed within a bath or other post-treatment process such that a hydrophobic or oleophobic layer is applied at least to a portion thereof. The embodiment illustrated in FIGS. 16-17 includes elements similar to the embodiment illustrated in FIGS. 1-7, for example: a container 410 comprising a containment shell 412, which encloses a contained volume 414 for the containment of fluids; and the transfer lid 430 further comprises an attachment collar 450 with threads 452 and gripping features 454.

According to another example embodiment, the transfer lid and the mating container (or at least the open threaded end thereof) are formed from polypropylene (PP). In example embodiments, polypropylene is non-polar and has an even distribution of electrons, and thus it will not be attracted to water (e.g., water is a polar molecule) and thereby naturally repelling the water (e.g., making it a hydrophobic material). In example embodiments, adding a textured surface increases the water droplet contact angle to greater than 150 degrees which indicates a superhydrophobic surface compared to >90 degree hydrophobic contact angle.

According to another example embodiment of the present invention, the transfer lids as described here can be configured such that the engagement interface (defined between the transfer lid and the container and/or the transfer port of the transfer lid and the syringe coupling) can comprise a texturized surface finish and/or a hydrophobic or oleophobic coating or layer, or for example, the material forming one or more of the components can be at least partially hydrophobic or oleophobic. For example, to further assist air ventilation and the prevention of fluids within the container from leaking through engagement interface, the hydrophobic or oleophobic layer (or characteristics of the material or component) acts as a nonpolar boundary that maximizes the bonding between molecules of the fluid within the container and minimizes the area of contact between the fluid molecules within the container and the nonpolar boundary of the hydrophobic or oleophobic layer. Thus, the nonpolar layer excludes molecules of the fluid from the surface thereof such that any fluids present at the micro-vented seal or engagement interface of the container with the transfer lid (or at the engagement interface of the transfer port with the syringe coupling) will generally bead and form droplets of fluid. As such, the fluid's reaction to the nonpolar boundary causes formation of the droplets such that the fluid molecules are incapable of a size reduction that would be capable of passing through one or more of the ventilation channels provided by the texturized surface finish. Accordingly, in one example embodiment, a texturized surface finish of between a VDI range of about 33-45 is provided. Optionally, other VDI values can be used as desired.

Figures 16, 17:
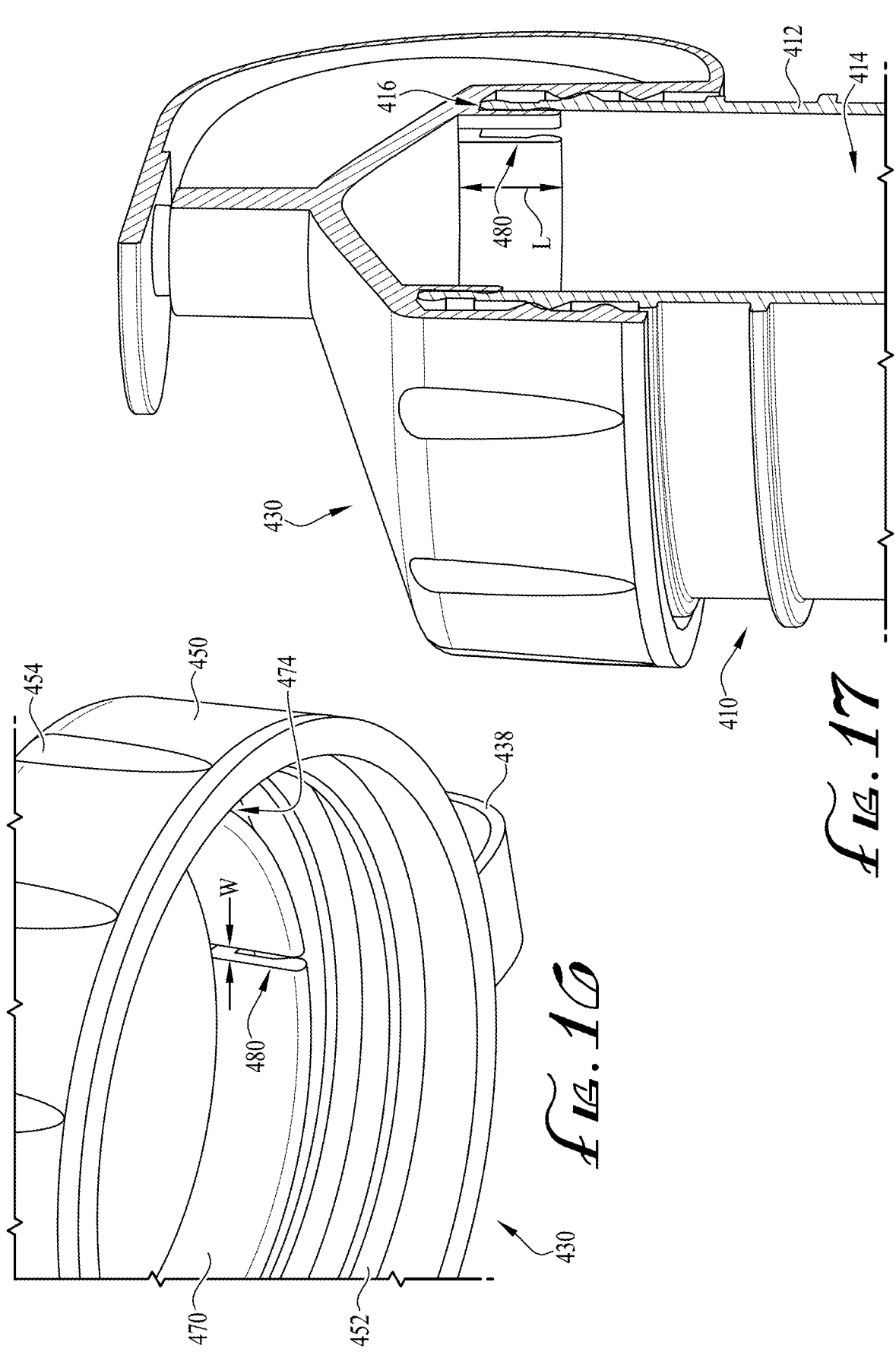
FIG. 16 shows a vented fluid transfer lid according to another example embodiment of the present invention.
FIG. 17 shows a perspective cross-sectional view of the vented fluid transfer lid of FIG. 16, showing the vented fluid transfer lid connected to an open threaded end of a bottle.

FIGS. 16-17 shows a vented fluid transfer lid 430 according to another example embodiment of the present invention. As shown, the transfer lid 430 comprises an outer circumferential collar 470 comprising at least one slit or air ventilation channel 480. According to one example embodiment, the ventilation channel 480 is sized and shaped such that when the outer circumferential collar 470 is engaged with an inner surface of the container (e.g., generally near the threaded open upper end 416), the size of the channel 480 is such that air is permitted to vent through the opening, but wherein one or more beads or droplets of fluid (caused by the fluid's reaction to the nonpolar boundary of the hydrophobic or oleophobic layer) are prevented from passing therethrough. In example embodiments, the channel 480 comprises a width W of between about 0.05-0.90 millimeters and a length L of between about 1.50-5.20 millimeters. For example, according to one embodiment, the width W is configured such that the beads or droplets of fluids comprise a dimension such that they are too large to pass through the channel 480, and thereby generally prevented from accumulating near the vent (e.g., by the presence of the nonpolar boundary). In some example embodiments, the collar 470 comprises an outer engagement surface 474 that can comprise an EDM surface finish applied thereto (in addition to the nonpolar boundary including the hydrophobic or oleophobic coating or layer).

Figure 19:
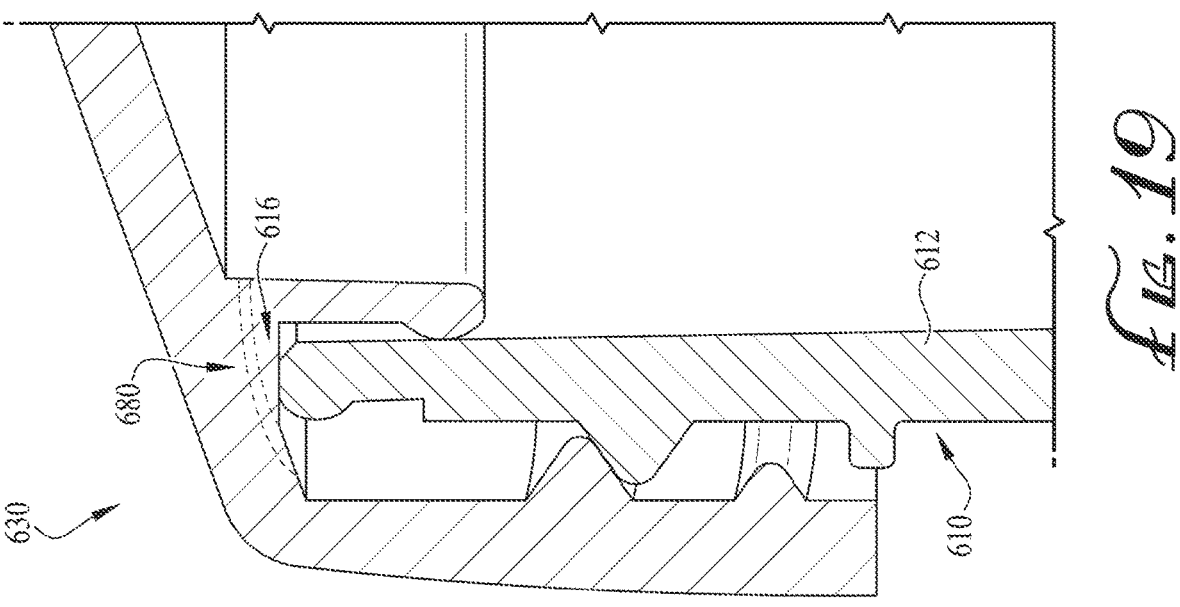
FIG. 19 shows a close-up cross-sectional view of a vented fluid transfer lid according to another example embodiment of the present invention, and showing an open threaded end of a bottle connected with the vented fluid transfer lid.
Figure 18:
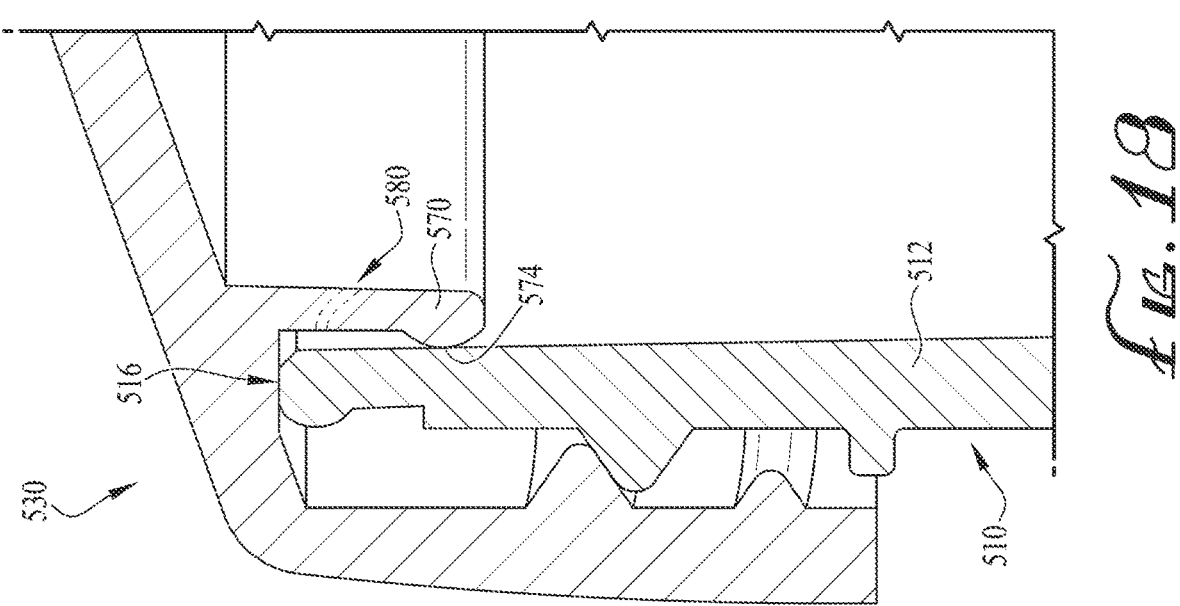
FIG. 18 shows a close-up cross-sectional view of a vented fluid transfer lid according to another example embodiment of the present invention, and showing an open threaded end of a bottle connected with the vented fluid transfer lid.

FIGS. 18-19 show transfer lids 530, 630 according to additional example embodiments of the present invention. According to example embodiments, one or more conduits or vent paths 580, 680 can be provided for permitting air ventilation. For example, as depicted, the vent paths 580, 680 can be configured such that the engagement or seal between the container 510, 610 with the transfer lid 530, 630 need not permit air to pass therethrough, for example, whereby the one or more vent paths 580, 680 permit air to pass therethrough for venting but prevent any liquid from passing through. For example, according to some embodiments, the vent paths 580, 680 are preferably sized to comprise a diameter of between about 0.05-0.90 millimeters and wherein a nonpolar boundary is provided at least near the respective vent path 580, 680 such that any fluid therein and generally present near the vent path 580, 680 forms one or more beads or droplets of fluid that are too large to pass through the vent path 580, 680. According to one example embodiment, the interior surface of the vent path 580, 680 also comprise the nonpolar boundary to further prevent fluid molecules from passing therethrough. The embodiment illustrated in FIGS. 16-17 includes elements similar to the embodiment illustrated in FIGS. 1-7, for example: the container 510 comprises a containment shell 512 and a threaded open upper end 516; a circumferential sealing flange or inner collar 570 with an outer circumferential face 574 projects from the top panel of the transfer lid 530; and the container 610 comprises a containment shell 612 and a threaded open upper end 616.

According to example embodiments of the present invention, with the container being inverted (e.g., oriented upside down) and having one of the transfer lids as described above attached thereto, a syringe fitted within the transfer port (or opening or lumen thereof) of the transfer lid can be used to draw or transfer fluids from the container and into the syringe (as similarly shown in FIGS. 7 and 10-11). Preferably, with the inner collar (or inner surface—see FIG. 11) having the texturized EDM surface finish and nonpolar boundary, air is permitted to pass through the seal or engagement interface and prevent a vacuum from forming within the container, and thus, facilitates the transfer of fluids from within the container into the syringe. Preferably, the nonpolar boundary causes any fluids present at the seal to form beads or droplets of fluid having a dimension that is too large to pass through the vented seal or engagement interface. Similarly, fluid from within the syringe can be transferred to the container, for example, wherein the discharging of fluids within the container (via the transfer lid and from the syringe) allows for air within the container to vent out of the container, for example, as the container begins to be filled with the fluid. In the same manner, the nonpolar boundary preferably causes any fluids present at the engagement interface to bead and form droplets having a size incapable of passing through the engagement interface. As similarly described above, other embodiments comprising one or more channels, vent paths and/or the texturized EDM surface preferably can function similarly to cause beading or the formation of fluid droplets when at least a portion thereof comprises the nonpolar boundary. According to other example embodiments, other connectors, fittings, couplings, etc. can be provided with the nonpolar boundary (or hydrophobic or oleophobic characteristics) to provide sufficient air ventilation without permitting fluids to pass therethrough.

As described above, one or more portions of the transfer lid, the container or other enteral couplings, connectors, fluid transfer members, syringes, etc. can comprise a hydrophobic or oleophibic coating or other surface treatment coating material(s) or layer(s) applied thereto. In some example embodiments, the hydrophobic material comprises high-density polyethylene (HDPE), which is coated with, impregnated with, or otherwise contains a hydrophilic material such as carboxymethylcellulose (CMC) or a polyacrylate. Alternative hydrophobic materials include but are not limited to polytetrafluoroethylene (PTFE), ultra-high molecular weight polyethylene (UHMWPE), Nylon 6, polypropylene (PP), polyvinylidine fluoride (PVDF) or polyethersulfone (PES). Alternatively, one or more surfaces thereof can comprise a matte finish, one or more micro-sized channels, laser drilled holes, a breathable cord, a superabsorbent, a one-way valve, or any other means or any combination of these, as appropriate and suitable for permitting ventilation. According to some example embodiments, a superhydrophobic material can be used, for example, a superhydrophobic nanocomposite coating including a xylene solvent containing titanium dioxide nanoparticles (NPs) functionalized with trimethoxypropyl silane. Alternatively, a mixture of functionalized NPs and dissolved PP pellets can be combined prior to injection molding, for example, such that the one or more components formed from the injection molding is at least partially, if not entirely, superhydrophobic. According to one example embodiment, at least a portion of the threads of the transfer lid and/or container can comprise a texturized EDM surface finish, for example, with or without other components or features thereof being texturized (or otherwise hydrophobic or syperhydrophobic) to further provide for air ventilation during the transfer of fluids between the container and the syringe.

According to yet another example embodiment of the present invention, one or more surfaces can be texturized by chemical etching. For example, according to one example form, a thermoplastic mold formed from carbon steel, stainless steel, aluminums, coppers, bronzes, etc. can be chemically etched, for example, such that a finish is formed on a portion of the mold to impress the etched finish on each part that is formed by the mold. In example embodiments, the chemical etching can be provided by ferric chloride (FeCl3) or nitric acid (HNO3). Optionally, other chemical etchants can be used as desired. In example embodiments, defining the area of the mold to be chemically etched is provided by masking off or protecting the areas that do not intend to comprise the texture from the etchant. In example embodiments, the masking can be provided by anything that resists the corrosive effects of the etchant and handling of the masking (during application and processing) can be used. In example embodiments, vinyl tapes and waxes, asphaltum or other mastics that can be easily applied by hand with paint brushes are generally used to protect the areas not intended to be etched. In some example embodiments, a tape or wax can be used to cover the broad areas and holes, and the paintable mastics are used for the detailed portions.

According to yet another example embodiment of the present invention, rather than providing a texturized surface finish by electrical discharge machining (EDM) or chemical etching (as described above), a desired texturized surface can alternatively be provided by sandblasting. For example, in a similar manner, the tool, mold, cavity or other tools used for molding the components or transfer lids as described herein can be texturized as desired, for example, by sandblasting the one or more portions of the tool or mold, and thus, forming a texturized surface thereon. Thus, as described above with respect to the texturized EDM surface finish, other methods or processes can be alternatively utilized to provide a desirable texturized surface finish, for example, by chemical etching, sandblasting, or other available surface texturing methods.

While the invention has been described with reference to example embodiments, it will be understood by those skilled in the art that a variety of modifications, additions and deletions are within the scope of the invention, as defined by the following claims.

What is claimed is:

1. An enteral fluid container comprising:
a containment shell; an open upper end including:
container threads, and
a container sealing lip defining an outwardly extending rounded surface, a shoulder positioned between the container threads and the outwardly extending rounded surface, and an angled inner container surface radially inward of the outwardly extending rounded surface; and
a vented transfer lid coupled to the open upper end and including:
a circular top panel comprising a transfer port extending from a central position on the top panel outwardly in a first or distal direction;
an attachment collar extending in a second or proximal direction from the top panel, an interior circumferential face of the attachment collar comprising lid threads for releasable engagement with the container threads; and
an inner collar projecting from the top panel of the transfer lid in the second or proximal direction, the inner collar being concentric with and spaced a distance inwardly from the attachment collar, and comprising an outer circumferential surface engaged with the angled inner container surface and having a texturized surface finish defining a VDI range of between about 24-42,
wherein the outer circumferential surface is configured to permit the venting of air into and out of the container at an engagement interface between the angled inner container surface and the outer circumferential surface.

2. The enteral fluid container of claim 1, wherein the transfer port is configured for compatible engagement with a coupling of a syringe,
wherein engagement of the coupling of the syringe with the transfer port defines an engagement interface comprising at least one vent path permitting the venting of air into and out of the container.

3. The enteral fluid container of claim 2, wherein the transfer port comprises a female enteral-only coupling configured to engage the coupling of the syringe comprising a male enteral-only coupling.

4. The enteral fluid container of claim 2, wherein the transfer port comprises a male ISO 80369-3 (as of Oct. 12, 2017) formatted coupling configured to engage the coupling of the syringe comprising a female ISO 80369-3 (as of Oct. 12, 2017) formatted coupling.

5. The enteral fluid container of claim 1, wherein at least a portion of the outer circumferential surface comprises an outer layer exhibiting oleophobic or hydrophobic characteristics.

6. The enteral fluid container of claim 1, wherein an oleophobic or hydrophobic coating is applied to at least a portion of the outer circumferential surface.

7. The enteral fluid container of claim 1, wherein an oleophobic or hydrophobic material is impregnated within at least a portion of the outer circumferential surface.

8. The enteral fluid container of claim 1, wherein the transfer port is configured for compatible engagement with a coupling of a syringe so that fluids can be transferred between the container and the syringe.

9. The enteral fluid container of claim 1, wherein the texturized surface finish is formed using electrical discharge machining (EDM).

10. The enteral fluid container of claim 1, wherein the inner collar defines a slit sized to permit gas to vent therethrough and inhibit one or more beads or droplets of fluid from passing therethrough.

11. The enteral fluid container of claim 10, wherein the slit defines a width of 0.05-0.90 millimeters.

12. The enteral fluid container of claim 10, wherein the slit defines a length of 1.50-5.20 millimeters.

13. The enteral fluid container of claim 10, wherein the slit exhibits oleophobic or hydrophobic characteristics.

\* \* \* \* \*